(12) United States Patent
Menzel Bueno et al.

(10) Patent No.: US 11,129,929 B2
(45) Date of Patent: *Sep. 28, 2021

(54) METHODS AND APPARATUSES USING UREA PERMSELECTIVE DIFFUSION THROUGH CHARGED MEMBRANES

(71) Applicants: Baxter International Inc., Deerfield, IL (US); Baxter Healthcare SA, Glattpark (CH)

(72) Inventors: Cristian Adolfo Menzel Bueno, Braine-l'Alleud (BE); Yuanpang Samuel Ding, Long Grove, IL (US); Rosa Yeh, Libertyville, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/673,451

(22) Filed: Nov. 4, 2019

(65) Prior Publication Data

US 2020/0061270 A1    Feb. 27, 2020

Related U.S. Application Data

(63) Continuation of application No. 15/265,058, filed on Sep. 14, 2016, now Pat. No. 10,463,776.

(Continued)

(51) Int. Cl.
*A61M 1/16*    (2006.01)
*A61M 1/34*    (2006.01)
(Continued)

(52) U.S. Cl.
CPC ........ *A61M 1/1696* (2013.01); *A61M 1/1603* (2014.02); *A61M 1/267* (2014.02); *A61M 1/282* (2014.02); *A61M 1/3472* (2013.01)

(58) Field of Classification Search
CPC ...... A61M 1/1696; A61M 1/284; A61M 1/28; A61M 1/14; A61M 1/1654
See application file for complete search history.

(56) References Cited

U.S. PATENT DOCUMENTS 3,472,766 A    10/1969 Shlomo
5,489,179 A    2/1996 Gabriel
(Continued)

FOREIGN PATENT DOCUMENTS

EP    1857439    11/2007
EP    2446908    5/2012
(Continued)

OTHER PUBLICATIONS

Lehmann, H. D., R. Marten, and C. A. Gullberg. "How to catch urea? Considerations on urea removal from hemofiltrate." Artificial Organs 5, No. 3 (1981): 278-285.

(Continued)

*Primary Examiner* — Ana M Fortuna
(74) *Attorney, Agent, or Firm* — K&L Gates LLP

(57) ABSTRACT

Methods and apparatuses for regenerating used dialysis fluid are described herein. In an embodiment, a regenerative dialysis fluid system includes a dialysis unit configured to generate used dialysis fluid including urea, a urea separation unit configured to separate at least a portion of the urea from the used dialysis fluid into a secondary fluid, and a urea removal unit configured to remove at least a portion of the urea from the secondary fluid and return the secondary fluid to the urea separation unit. In an embodiment, the urea separation unit includes a membrane separating a dialysis fluid chamber from a urea chamber, the membrane including at least one of: (i) a positive charge to prevent positive ions (Continued)

from transporting across the membrane; and (ii) a negative charge to prevent negative ions from transporting across the membrane.

19 Claims, 12 Drawing Sheets

Related U.S. Application Data

(60) Provisional application No. 62/273,863, filed on Dec. 31, 2015, provisional application No. 62/373,108, filed on Aug. 10, 2016.

(51) Int. Cl.
*A61M 1/26* (2006.01)
*A61M 1/28* (2006.01)

(56) References Cited

U.S. PATENT DOCUMENTS

| | | |
|---|---|---|
| 5,944,684 A | 8/1999 | Roberts et al. |
| 6,284,124 B1 | 9/2001 | DiMascio |
| 6,506,305 B2 | 1/2003 | Morita et al. |
| 7,033,498 B2 | 4/2006 | Wong |
| 7,867,214 B2 | 1/2011 | Childers et al. |
| 8,715,221 B2 | 5/2014 | Curtin et al. |
| 8,858,792 B2 | 10/2014 | Ding |
| 8,876,753 B2 | 11/2014 | Roberts et al. |
| 2005/0194304 A1 | 9/2005 | Paolis |
| 2008/0011664 A1 | 1/2008 | Karoor |
| 2009/0114595 A1 | 5/2009 | Wallenas |
| 2010/0010429 A1* | 1/2010 | Childers ............ A61M 1/288 604/29 |
| 2010/0234795 A1* | 9/2010 | Wallenas ........... A61M 1/3482 604/29 |
| 2011/0048949 A1* | 3/2011 | Ding ................. A61M 1/1696 204/543 |
| 2012/0145550 A1 | 6/2012 | Kim |
| 2012/0273354 A1 | 11/2012 | Orhan |
| 2013/0213891 A1* | 8/2013 | Karoor ................ A61M 1/28 210/646 |
| 2013/0274642 A1* | 10/2013 | Soykan ............... A61B 5/0452 604/5.01 |
| 2014/0336568 A1 | 11/2014 | Wong |
| 2016/0375190 A1* | 12/2016 | Blatter .................. A61M 1/28 604/28 |
| 2017/0043078 A1* | 2/2017 | Thiebaud ........... A61M 1/3472 |
| 2017/0189595 A1 | 7/2017 | Ding |
| 2017/0348472 A1 | 12/2017 | Pesenti |
| 2018/0140765 A1* | 5/2018 | Wallen S ............... B01J 20/22 |

FOREIGN PATENT DOCUMENTS

| | | |
|---|---|---|
| EP | 2862584 | 4/2015 |
| GB | 2403166 | 12/2004 |
| WO | 2012060700 | 5/2012 |
| WO | 2015124716 | 8/2015 |
| WO | WO-2020218571 A1 * | 10/2020 ............. A61M 1/16 |

OTHER PUBLICATIONS

Ozaki, Hiroaki, and Huafang Li. "Rejection of organic compounds by ultra-low pressure reverse osmosis membrane." Water Research 36, No. 1 (2002): 123-130.

Huang, Chuanhui, and Tongwen Xu. "Electrodialysis with bipolar membranes for sustainable development." Environmental Sscience & Technology 40, No. 17 (2006): 5233-5243.

Xu, Jun, Zhi Wang, Jixiao Wang, and Shichang Wang. "Positively charged aromatic polyamide reverse osmosis membrane with high anti-fouling property prepared by polyethylenimine grafting." Desalination 365 (2015): 398-406.

Cui, Yue, Zhi-Kan Yao, Ke Zheng, Shi-Yuan Du, Bao-Ku Zhu, Li-Ping Zhu, and Chun-Hui Du. "Positively-charged nanofiltration membrane formed by quaternization and cross-linking of blend PVC/P (DMA-co-MMA) precursors." Journal of Membrane Science 492 (2015): 187-196.

Wang, Xiao-lei, Jun-fu Wei, Zhao Dai, Kong-yin Zhao, and Huan Zhang. "Preparation and characterization of negatively charged hollow fiber nanofiltration membrane by plasma-induced graft polymerization." Desalination 286 (2012): 138-144.

International Search Report and Written Opinion issued in related International Patent Application No. PCT/US2016/0686695 dated Mar. 31, 2017.

* cited by examiner

METHODS AND APPARATUSES USING UREA PERMSELECTIVE DIFFUSION THROUGH CHARGED MEMBRANES

PRIORITY CLAIM

The present application claims priority to and the benefit as a continuation application of U.S. patent application Ser. No. 15/265,058, filed Sep. 14, 2016, now U.S. Pat. No. 10,443,776, entitled "Methods and Apparatuses using Urea Permselective Diffusion Through Charged Membranes", which claims priority to U.S. Provisional Application No. 62/273,863, filed Dec. 31, 2015, entitled, "Devices for Urea Electrolysis and Methods of Using Same", and to U.S. Provisional Application No. 62/373,108, filed Aug. 10, 2016, entitled, "Methods and Apparatuses using Urea Permselective Diffusion Through Charged Membranes", the entire contents of each of which are incorporated herein by reference and relied upon.

BACKGROUND

Due to disease or insult or other causes, the renal system may fail. In renal failure of any cause, there are several physiological derangements. The balance of water, ions (e.g., $Na^+$, $K^+$, $Cl^-$, $Ca^{2+}$, $PO_4^{2-}$) and the excretion of daily metabolic load of fixed hydrogen ions is no longer possible with renal failure. Further, during renal failure, toxic end products of nitrogen metabolism including, for example, urea, creatinine, uric acid, and others may accumulate in the patient's blood and tissues.

Several types of dialysis treatment have been devised (e.g., peritoneal dialysis, hemodialysis, hemofiltration, and hemodiafiltration) for the removal of toxic end products of nitrogen metabolism from blood. These types of dialysis treatment rely on diffusion of urea across a membrane and/or enzymatic degradation of urea. However, degradation of urea is problematic in that it produces toxic end products such as ammonium that must be removed and/or trapped (or treatment fluid discarded) to ensure that they are not returned to a patient. Sorbents are often employed during dialysis to bind such toxic end products. These sorbents are expensive and add bulk to a dialysis system, making them less suitable to being used in portable or wearable applications.

A need accordingly exists for improved regenerative dialysis systems that remove urea from blood to reduce or eliminate the risk that toxic end products will be present in the regenerated dialysis fluid.

SUMMARY

When dialysis fluid is cleansed of urea so that it may be reused, the urea cleansing may create toxic byproducts which then need to be removed from the dialysis fluid. The present disclosure in various embodiments uses a charged membrane to separate urea from a dialysis fluid circuit before the urea is cleansed from the system. By removing the urea into a secondary fluid circuit separate from the dialysis fluid, the present disclosure reduces the risk of the toxic byproducts remaining in the dialysis fluid and avoids the depletion of dialysis fluid constituents.

The charged membrane of the present disclosure uses the principles of electrostatic repulsion and/or size exclusion to separate urea from used dialysis fluid. The charged membrane may include a negative charge to prevent negative ions from penetrating the membrane and/or a positive charge to prevent positive ions from penetrating the membrane. Because urea is uncharged, urea may be filtered from dialysis fluid through the membrane, while dialysis fluid constituents, which are charged, are prevented from penetrating the membrane. The urea may then be cleansed or removed outside of the dialysis fluid circuit so that toxic byproducts of the urea cleansing do not leach into the dialysis fluid.

The regenerative dialysis fluid system disclosed herein may be used to regenerate dialysis fluid for a blood treatment or a peritoneal dialysis treatment. The blood treatment can be, for example, a hemodialysis, hemofiltration or hemodiafiltration treatment. The peritoneal dialysis treatment can be, for example, a continuous ambulatory peritoneal dialysis ("CAPD") treatment, an automated peritoneal dialysis ("APD") treatment, or a batch treatment. The treatment may have continuous or non-continuous ("batch") flow.

The regenerative dialysis fluid system disclosed herein may also use a plurality of different mechanisms to remove urea from dialysis fluid after the urea has passed through the charged membrane. Urea may be removed, for example, via a chemical adsorption unit, an electrooxidation unit and/or an enzymatic oxidation unit.

In a first general embodiment, which may be used in combination with any other embodiment described herein unless specified otherwise, a regenerative dialysis fluid system includes a dialysis unit configured to generate used dialysis fluid including urea, a urea separation unit configured to separate at least a portion of the urea from the used dialysis fluid into a secondary fluid, and a urea removal unit configured to remove at least a portion of the urea from the secondary fluid and return the secondary fluid to the urea separation unit.

In a second general embodiment, which may be used in combination with any other embodiment described herein unless specified otherwise, the dialysis unit is configured to clean blood to generate the used dialysis fluid.

In a third general embodiment, which may be used in combination with any other embodiment described herein unless specified otherwise, the dialysis unit is a peritoneal dialysis unit.

In a fourth general embodiment, which may be used in combination with any other embodiment described herein unless specified otherwise, the urea separation unit includes a dialysis fluid chamber, a urea chamber and a membrane separating the dialysis fluid chamber from the urea chamber, the dialysis fluid chamber receiving the used dialysis fluid generated by the dialysis unit, the urea chamber outputting the secondary fluid with urea to the urea removal unit.

In a fifth general embodiment, which may be used in combination with any other embodiment described herein unless specified otherwise, an outlet of the dialysis unit is in fluid communication with an inlet of the dialysis fluid chamber, and an inlet of the dialysis unit is in fluid communication with an outlet of the dialysis fluid chamber.

In a sixth general embodiment, which may be used in combination with any other embodiment described herein unless specified otherwise, an outlet of the urea chamber is in fluid communication with an inlet of the urea removal unit, and an inlet of the urea chamber is in fluid communication with an outlet of the urea removal unit.

In a seventh general embodiment, which may be used in combination with any other embodiment described herein unless specified otherwise, the membrane includes at least one of: (i) a positive charge to prevent positive ions from transporting across the membrane between the dialysis fluid chamber and the urea chamber; and (ii) a negative charge to prevent negative ions from transporting across the membrane between the dialysis fluid chamber and the urea chamber.

In an eighth general embodiment, which may be used in combination with any other embodiment described herein unless specified otherwise, the membrane includes pores sized between about 5 nm and 10 μm.

In a ninth general embodiment, which may be used in combination with any other embodiment described herein unless specified otherwise, the system includes at least one pump and a control unit configured to control the at least one pump to pump fluid between the dialysis unit, the urea separation unit and the urea removal unit.

In a tenth general embodiment, which may be used in combination with any other embodiment described herein unless specified otherwise, the urea removal unit includes at least one of a chemical adsorption device, an electrooxidation device or an enzymatic oxidation device.

In an eleventh general embodiment, which may be used in combination with any other embodiment described herein unless specified otherwise, the urea removal unit is configured to collect or discard the urea removed from the secondary fluid.

In a twelfth general embodiment, which may be used in combination with any other embodiment described herein unless specified otherwise, a urea separation unit includes a dialysis fluid chamber configured to receive a continuous flow of dialysis fluid, a urea chamber configured to receive a continuous flow of a secondary fluid, and a membrane separating the dialysis fluid chamber from the urea chamber, the membrane including at least one of: (i) a positive charge to prevent positive ions from transporting across the membrane between the dialysis fluid chamber and the urea chamber; and (ii) a negative charge to prevent negative ions from transporting across the membrane between the dialysis fluid chamber and the urea chamber.

In a thirteenth general embodiment, which may be used in combination with any other embodiment described herein unless specified otherwise, the membrane includes an anion exchange membrane ("AEM") and a cation exchange membrane ("CEM"), the AEM providing the positive charge and the CEM providing the negative charge.

In a fourteenth general embodiment, which may be used in combination with any other embodiment described herein unless specified otherwise, the membrane maintains the positive charge and the negative charge.

In a fifteenth general embodiment, which may be used in combination with any other embodiment described herein unless specified otherwise, the urea separation unit includes a blood chamber in addition to the dialysis fluid chamber and the urea chamber, wherein the membrane is a first membrane, and which includes a second membrane configured to filter waste fluid from blood in the blood chamber into the dialysis fluid chamber.

In a sixteenth general embodiment, which may be used in combination with any other embodiment described herein unless specified otherwise, the dialysis fluid chamber is located between the first membrane and the second membrane.

In a seventeenth general embodiment, which may be used in combination with any other embodiment described herein unless specified otherwise, the dialysis fluid chamber is located between the blood chamber and the urea chamber.

In an eighteenth general embodiment, which may be used in combination with any other embodiment described herein unless specified otherwise, a method of regenerating used dialysis fluid includes pumping, under control of a control unit, used dialysis fluid including urea against a charged membrane such that at least a portion of the urea flows across the charged membrane into a secondary fluid, and removing, under control of the control unit, at least a portion of the urea from the secondary fluid.

In a nineteenth general embodiment, which may be used in combination with any other embodiment described herein unless specified otherwise, the method includes pumping, under control of the control unit, blood against a waste membrane to remove waste fluid into the used dialysis fluid.

In a twentieth general embodiment, which may be used in combination with any other embodiment described herein unless specified otherwise, the method includes pumping, under control of the control unit, the used dialysis fluid through an adsorption device before pumping the used dialysis fluid against the charged membrane.

In a twenty-first general embodiment, which may be used in combination with any other embodiment described herein unless specified otherwise, the method includes automatically adjusting, under control of the control unit, flow of the urea across the charged membrane into the secondary fluid based on feedback from a sensor.

In a twenty-second general embodiment, which may be used in combination with any other embodiment described herein unless specified otherwise, the method includes removing, under control of the control unit, the urea from the secondary fluid by at least one of chemical adsorption, electrooxidation or enzymatic oxidation.

In a twenty-third embodiment, which may be combined with any other embodiment discussed herein unless specified otherwise, any one, or more, or all of a control unit, one or more pumps, valves, pH sensors, and/or flowmeters may be employed to produce a desired flow regime.

In a twenty-fourth embodiment, any of the structure, functionality and alternative embodiments associated with any of FIGS. 1 to 10 may be used with any of the structure, functionality and alternative embodiments associated with any one or more other FIGS. 1 to 10.

In light of the present disclosure and the above aspects, it is an advantage of the present disclosure to provide a system that is able to regenerate dialysis fluid.

It is another advantage of the present disclosure to remove urea from dialysis fluid without the risk that toxic byproducts from the urea removal will diffuse or flow back to the dialysis fluid.

It is a further advantage of the present disclosure to remove urea from dialysis fluid without depleting dialysis fluid constituents.

It is still a further advantage of the present disclosure to provide a system that is able to perform multiple treatments and reduce or minimize the need to replace components of the system.

The advantages discussed herein may be found in one, or some, and perhaps not all of the embodiments disclosed herein. Additional features and advantages are described herein, and will be apparent from, the following Detailed Description and the figures.

The foregoing summary, as well as the following detailed description of the disclosure, will be better understood when read in conjunction with the appended figures. For the purpose of illustrating the disclosure, shown in the figures are embodiments which may be presently preferred. It should be understood, however, that the disclosure is not limited to the precise arrangements, examples and instrumentalities shown. Additionally, the embodiments described and claimed herein do not have to have each of the features and advantages listed herein.

DETAILED DESCRIPTION

Figure 1:
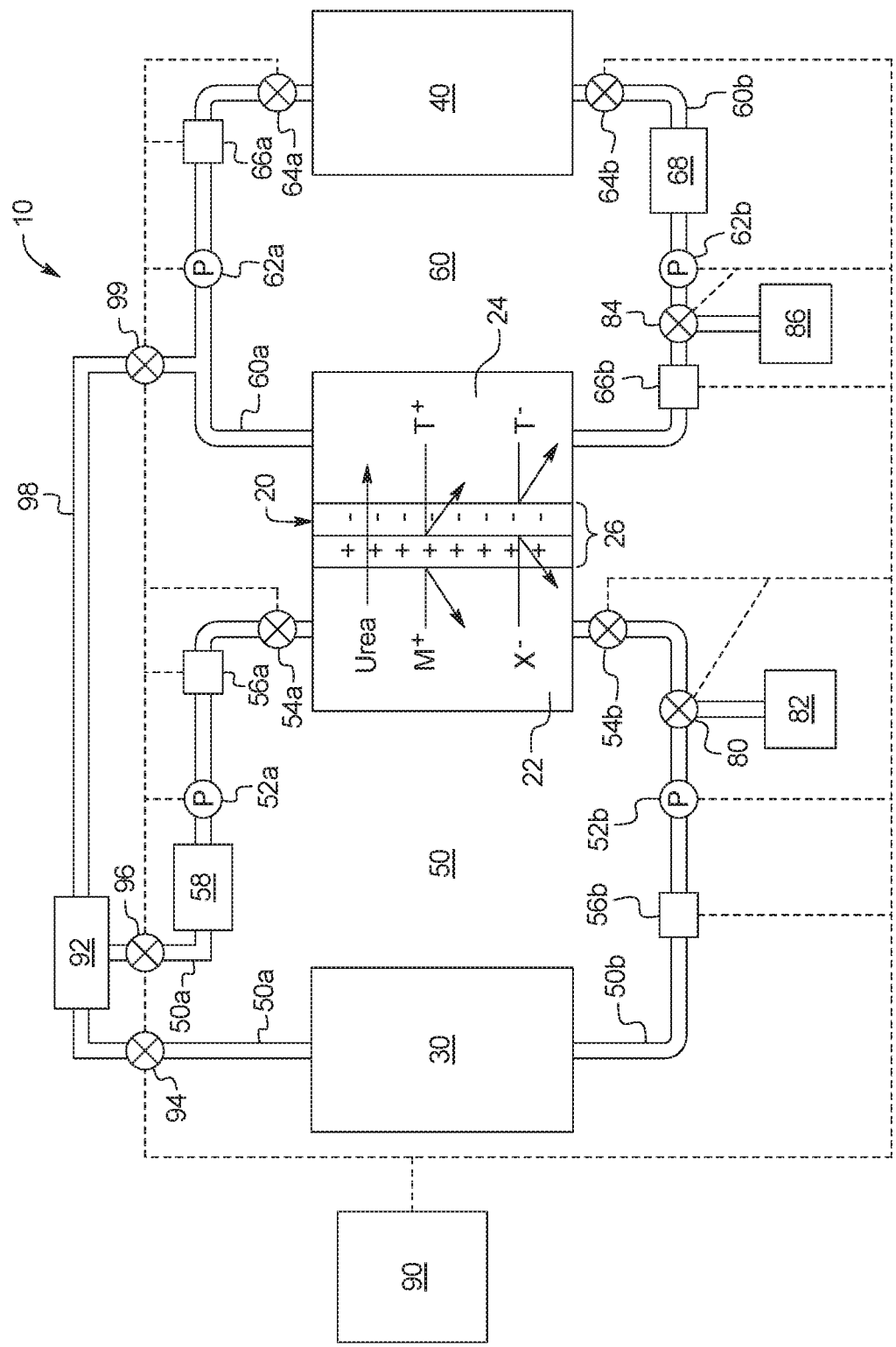
FIG. 1 illustrates an example embodiment of a regenerative dialysis fluid system according to the present disclosure.

FIG. 1 illustrates an example embodiment of a regenerative dialysis fluid system 10 according to the present disclosure. In the illustrated embodiment, system 10 includes a urea separation unit 20, a dialysis unit 30, and a urea removal unit 40. In use, urea separation unit 20 receives used dialysis fluid containing urea from dialysis unit 30, separates the urea from the used dialysis fluid, and directs the urea to urea removal unit 40, allowing the urea to be removed from system 10 by urea removal unit 40. Specific example embodiments of dialysis unit 30 and urea removal unit 40 are discussed in more detail below. System 10 is advantageous, for example, because urea may be separated from the main dialysis fluid circuit before it is removed from system 10, which reduces the risk of toxic byproducts from the urea removal leaching into the dialysis fluid circuit. System 10 also avoids the depletion (e.g., co-adsorption, oxidation) of dialysis fluid constituents during urea removal.

Urea separation unit 20 includes a used dialysis fluid chamber 22 and a urea chamber 24, which are separated by a urea permselective membrane 26 with at least one of a positive charge and a negative charge. In an embodiment, membrane 26 has a bipolar structure with a positive charge and a negative charge. In another embodiment, membrane 26 may be charged on one side with a positive charge and on the other side with a negative charge. In a further embodiment, urea permselective membrane 26 may be charged with a single charge (e.g., positive charge or negative charge) on one or both faces. The positive and negative charges may be applied to membrane 26, for example, via the membrane composition, functionalization and/or surface treatment. For example, a positively charged membrane may be formed by quaternization and cross-linking of polyvinyl chloride ("PVC")poly(dimethylaminoethyl methacrylate-co-methyl methacrylate) precursors, or by polyethylenimine grafting. A negatively charged membrane may be formed by plasma-induced graft polymerization.

In still another embodiment, the negatively charged membrane may be a polyamide membrane derived from carboxylic acid or chloride acid containing monomers or precursors. In a further embodiment, the negatively charged membrane may be converted to be positively charged, via derivation of the carboxylic groups. It is to be understood that the methods and apparatuses using the urea permselective membrane according to the present disclosure may incorporate other suitable ways of obtaining the positive and negative charges.

In another embodiment, membrane 26 may include an anion exchange membrane ("AEM") and/or a cation exchange membrane ("CEM") to provide the positive and negative charges. Membrane 26 may be formed, for example, from a dialysis membrane, an ultrafiltration membrane, a microfiltration membrane, a quaternized membrane, an ethoxilated polyamide membrane or a bipolar membrane. According to certain non-limiting embodiments, membrane 26 has pore sizes between 5 nanometers ("nm") and 10 micrometers ("µm"). According to further non-limiting embodiments, membrane 26 may have one or more pore size appropriate for filtering out dialysate solutes such as glucose and organic molecules. According to certain non-limiting embodiments, membrane 26 may be resuable, for example, by washing with a high or low pH solution to remove fouling. In an embodiment, membrane 26 may be backflushed with pure water or a disinfectant solution such as formaldehyde or bleach to remove fouling. In some embodiments, membrane 26 may be removable from the urea separation unit 20. In this way, membrane 26 can be removed, regenerated, and installed back onto the urea separation unit, or fitted to a new urea separation unit.

Membrane 26 uses electrostatic repulsion and/or size exclusion to separate urea from used dialysis fluid that continuously passes through dialysis fluid chamber 22. Under the principle of electrostatic repulsion, positive ions may not cross membrane 26 due to the positive charge of membrane 26, and negative ions may not cross membrane 26 due to the negative charge of membrane 26. Because urea particles are uncharged, urea may be filtered across membrane 26 from dialysis fluid chamber 22 to urea chamber 24 by diffusion when there is a concentration and/or pressure difference across membrane 26. The urea separation may be performed under isobaric (i.e., at a constant pressure) and low transmembrane pressure conditions. According to certain non-limiting embodiments, membrane 26 does not require electrodes to cause the urea separation across membrane 26. According to further non-limiting embodiments, the urea separation process is mainly controlled by diffusion (i.e., urea concentration gradient) to transport urea across membrane 26, rather than by applying an electric field.

In FIG. 1, the used dialysis fluid pumped into dialysis fluid chamber 22 is illustrated as a salt solution MX, which contains positively charged ions (M+) and negatively charged ions (X−). In an embodiment, the salt solution (MX) is sodium chloride (NaCl) (wherein, M=Na, X=Cl). As illustrated, the positively charged M+ ions may not cross membrane 26 due to the positive charge of membrane 26, and the negatively charged X− ions may not cross membrane 26 due to the negative charge of membrane 26. Uncharged particles in the salt solution MX however may be transported across membrane 26 by diffusion when there is a concentration difference across membrane 26 without transporting the salt solution itself across membrane 26.

In FIG. 1, T+ and T− represent potentially toxic species created when urea is cleansed from system 10 by urea removal unit 40. The potentially toxic species may include, for example, heavy metals, urea oxidation byproducts, chlorinated species and/or leachables from an adsorption sorbent. The positively charged T+ ions may not cross membrane 26 into dialysis fluid chamber 22 due to the positive charge of membrane 26, while the negatively charged T− ions may not cross membrane 26 into dialysis fluid chamber 22 due to the negative charge of membrane 26. Membrane 26 therefore not only prevents useful dialysis constituents from crossing into urea chamber 24 from dialysis fluid chamber 22, it also prevents toxins from passing into the regenerated dialysis fluid in dialysis fluid chamber 22 from urea chamber 24.

In an embodiment, membrane 26 includes pores sized between about 5 nm and 10 μm to filter urea from used dialysis fluid using size exclusion in addition to electrostatic repulsion. The size exclusion may be used to prevent uncharged particles other than urea from being filtered across membrane 26. For example, glucose in peritoneal dialysis fluid is uncharged, but it is undesirable for the glucose concentration of the peritoneal dialysis fluid to be changed as the peritoneal dialysis solution is regenerated by urea separation unit 20. Since glucose molecules are larger than urea molecules, the pore size of membrane 26 may be constructed to allow the passage of urea, while preventing the passage of glucose. Alternatively, the passage of glucose across membrane 26 may be prevented by maintaining the concentration of glucose in urea chamber 24 to be the same as the concentration of glucose in dialysis fluid chamber 22. In another embodiment, size exclusion may be used to prevent creatinine, uric acid, or proteins in a hemodialysis fluid for a blood treatment from passing through membrane 26.

Dialysis fluid circuit 50 places dialysis unit 30 in fluid communication with dialysis fluid chamber 22 of urea separation unit 20, and provides a continuous flow of dialysis fluid through dialysis fluid chamber 22. In the illustrated embodiment, dialysis fluid circuit 50 may be filled initially with dialysis fluid from dialysis fluid source 92. In the illustrated embodiment, dialysis fluid source 92 is placed inline with dialysis fluid circuit 50 as part of used dialysis fluid flowpath 50*a*. Alternatively, dialysis fluid source 92 may be placed inline with regenerated dialysis fluid flowpath 50*b*. In an embodiment, dialysis fluid source 92 may initially include six liters of dialysis fluid to be pumped through dialysis fluid circuit 50. By opening valves 94, 96 and operating pump 52*a* and/or pump 52*b*, the dialysis fluid from dialysis fluid source 92 is pumped through dialysis fluid circuit 50 to prime dialysis fluid circuit 50 for treatment. Placing source 92 inline with dialysis fluid circuit 50 allows all of the fresh fluid from source 92 to be used over the course of a treatment. For example, if source 92 includes six liters of fresh fluid and dialysis fluid circuit 50 requires three liters for priming, three liters may accordingly remain in source 92 (e.g., for an HD treatment). Those three liters however will mix with the regenerated dialysis fluid over treatment due to the inline relationship of source 92. Thus, the full osmotic potential of the fresh fluid in source 92 will be consumed over the course of treatment.

Applying the same example to a PD treatment, the patient's peritoneum will be filled initially from source 92, e.g., using one to two liters. Circuit 50 consumes, e.g. three liters, leaving one or two liters in source 92, which mixes during treatment to use the full osmotic potential of the fresh fluid of source 92.

It should be appreciated that urea circuit 60 also needs to be primed at the beginning of treatment. It is accordingly desirable to keep the volume of urea circuit 60 (and dialysis fluid circuit 50) as small as possible, so enough fluid remains for the patient. Valve 99 is provided for enabling pumps 62*a* and 62*b* to pull fresh fluid initially from source 92 for priming. Valve 99 may be closed during treatment.

Circuits 50 and 60 and/or source 92 may be provided with a hydophobic vent as needed to displace air from circuits 50 and 60 during priming. Source bag or container 92 also provides an area to store ultrafiltrate ("UF") removed from the patient over the course of treatment. The total amount of UF removed from the patient may be determined by weighing source 92 after priming circuits 50 and 60 (and filling the patient for PD) but before treatment begins, and subtracting that weight from the weight of source 92 at the end of treatment.

While source 92 is inline in one embodiment, source 92 is connected alternatively via a single line, one each to circuits 50 and 60. Here, only one valve 94 or 96 is needed and that valve may be opened periodically during treatment to enable new fresh fluid to be pulled from source 92 and mixed into circuit 50, and to allow UF to be pushed into source 92.

The description involving source 92, priming and the operation of valves 94, 96 and 99, including all alternatives, is applicable to each of the embodiments and drawings described herein.

In use, used dialysis fluid containing urea is pumped by pump 52*a* from dialysis unit 30 to dialysis fluid chamber 22 via used dialysis fluid flowpath 50*a* of dialysis fluid circuit 50. After urea separation unit 20 removes at least a portion of the urea from the used dialysis fluid flowing through dialysis fluid chamber 22 by filtering the urea across urea permselective membrane 26 (and first adsorption device 58 removes other toxins, as further explained below), the urea-free regenerated dialysis fluid may be recirculated back to dialysis unit 30 by pump 52*b* through regenerated dialysis fluid flowpath 50*b* of dialysis fluid circuit 50 so that the urea-free regenerated dialysis fluid may be reused by dialysis unit 30.

In an embodiment, dialysis fluid circuit 50 may include a valve 80 and a fluid bag 82. In the illustrated embodiment, valve 80 is a three-way valve which allows fluid from fluid bag 82 to be added to dialysis fluid circuit 50. In an embodiment, the fluid in fluid bag 82 may be, for example, dialysis fluid that may be added to dialysis fluid circuit 50 if more fluid is needed in dialysis fluid circuit 50 due to the loss of fluid through membrane 26. In another embodiment, the fluid in fluid bag 82 may be used to raise or lower the pH of dialysis fluid flowing through dialysis fluid circuit 50 or to add electrolytes to the dialysis fluid flowing through dialysis fluid circuit 50. Fluid bag 82 may also be used to drain fluid from dialysis fluid circuit 50 if necessary. In an embodiment, multiple valves 80 and fluid bags 82 may be fluidly connected to dialysis fluid circuit 50 at used dialysis fluid flowpath 50*a* and/or regenerated dialysis fluid flowpath 50*b*.

Urea circuit 60 places urea removal unit 40 in fluid communication with urea chamber 24 of urea separation unit 20, and provides a continuous flow of secondary fluid through urea chamber 24. In an embodiment, dialysis fluid source 92 can be fluidly connected to urea circuit 60 via bypass flowpath 98, which allows dialysis fluid from dialysis fluid source 92 to flow into urea circuit 60 and act as secondary fluid within urea circuit 60. In the illustrated embodiment, valve 99 is opened before treatment begins to fill urea circuit 60 with dialysis fluid (e.g., one liter) to prepare urea circuit 60 for treatment. In an alternative embodiment, a separate source of fluid can branch off of urea circuit 60 or be placed inline with urea circuit 60 to supply fluid initially to urea circuit 60. In another alternative embodiment, urea circuit 60 can be filled with water prior to treatment.

In use, secondary fluid containing the urea removed across membrane 26 from dialysis fluid chamber 22 to urea chamber 24 may be pumped by pump 62a to urea removal unit 40 via first flowpath 60a of urea circuit 60. After being cleansed of at least a portion of the urea by urea removal unit 40, the urea-free secondary fluid may be recirculated back to urea chamber 24 of urea separation unit 20 by pump 62b through second flowpath 60b of urea circuit 60 so that the secondary fluid may be used to circulate additional urea from urea chamber 24 to urea removal unit 40. In an embodiment, the secondary fluid circulating through urea circuit 60 includes an isoosmolar solution which prevents water transport. An isoosmolar dextrose solution, for example, may be used to avoid dextrose diffusion across membrane 26 so that the only mass transfer across membrane 26 is by the diffusion of urea. Electrolytes may also be added to urea circuit 60 to ensure isoosmolar conditions. In another embodiment, the secondary fluid may be water or an electrolyte fluid.

In an embodiment, urea circuit 60 may include a valve 84 and a fluid bag 86. In the illustrated embodiment, valve 84 is a three-way valve which allows excess fluid to be drained from urea circuit 60 into fluid bag 86. In an embodiment, fluid bag 82 may include secondary fluid, and valve 84 may allow secondary fluid from fluid bag 86 to be added to urea circuit 60. In another embodiment, the fluid in fluid bag 86 may be used to raise or lower the pH of secondary fluid flowing through urea circuit 60 or to add electrolytes to the secondary fluid flowing through urea circuit 60. In an embodiment, multiple valves 84 and fluid bags 86 may be fluidly connected to urea circuit 60 at first flowpath 60a and/or second flowpath 60b.

In all continuous flow treatments, the dialysis fluid flowing through dialysis fluid circuit 50 is heated to a desired temperature. Dialysis fluid circuit can therefore include an inline heater that heats dialysis fluid to the desired temperature as the fluid flows continuously past the heater. The inline heaters may be resistive, inductive, radiant, infrared, and combinations thereof.

As illustrated, system 10 may include one or more pump 52a, 52b, 62a, 62b and/or a plurality of valves 54a, 54b, 64a, 64b, 80, 84, 94, 96, 99 that control fluid flow along the respective flowpaths. Pumps 52a, 52b, 62a, 62b may for example be peristaltic pumps or volume membrane pumps. Valves 54a, 54b, 64a, 64b, 80, 84, 94, 96, 99 may for example be variable fluid orifice valves, solenoid valves or other valves known to those of ordinary skill in the art. In the illustrated embodiment, the pumps 52a, 52b, 62a, 62b and valves 54a, 54b, 64a, 64b, 80, 84, 94, 96, 99 are electrically connected to a control unit 90. Control unit 90 may include one or more processor and memory programmed to control pumps 52a, 52b, 62a, 62b and the valves 54a, 54b, 64a, 64b, 80, 84, 94, 96, 99. Control unit 90 may control the pumps 52a, 52b, 62a, 62b and valves 54a, 54b, 64a, 64b, 80, 84, 94, 96, 99 to control transmembrane pressure. The flowrates through dialysis fluid chamber 22 and urea chamber 24 may also be increased by control unit 90 to facilitate urea diffusion. In an embodiment, the flowrates through dialysis fluid circuit 50 and urea circuit 60 are about 400 mL/min. In another embodiment, control unit 90 may be used to adjust flow rates so that the Reynolds number on both sides of membrane 26 reduces any stagnant layer formation at a membrane/fluid interface, which may limit the mass transport of urea across membrane 26. In an embodiment, control unit 90 may cause a turbulent flow with a high Reynolds number against one or both sides of membrane 26 so that a stagnant layer does not form on membrane 26. In other embodiments, techniques such as using pulsatile flow, a baffle design and/or mechanical vibrations, agitations or perturbations can be used to create turbulence near membrane 26 to minimize flow stagnation and enhance mass transfer across membrane 26. The methods and apparatuses described herein are not limited in this regard.

In an embodiment, any one or more or all of valves 54a, 54b, 64a, 64b, 80, 84, 94, 96, 99 may alternatively be solenoid valves that operate with control unit 90 so that they are opened a specified amount of time to achieve appropriate flow distributions through system 10. In a further embodiment, one or more valves 54a, 54b, 64a, 64b, 80, 84, 94, 96, 99 may be replaced with a balance chamber that operates with its own valves. Each balance chamber may include a first compartment and a second compartment separated by a flexible membrane. When a first inlet solenoid valve opens to allow the first compartment to fill with fluid, the flexible membrane is pushed into the second compartment to expel like fluid from the second compartment through an opened second outlet solenoid valve. When a second inlet solenoid valve opens to allow the second compartment to fill with fluid, the flexible membrane is pushed into the first compartment to expel like fluid from the first compartment through an opened first outlet solenoid valve. Because the volume of the first and second compartments is known, control unit 90 may precisely meter fluid through the flowpaths by toggling the solenoid valves of the balance chamber between the first compartment and the second compartment and control the flow rate by controlling how often the inlet and outlet valves are cycled.

In an embodiment, system 10 includes one or more sensor 56a, 56b, 66a, 66b to monitor fluid flow at any desired one or more location within the respective flowpaths of system 10 and provide feedback to control unit 90. In an embodiment, one or more of the sensors 56a, 56b, 66a, 66b may be a flowrate sensor, which provides feedback to control unit 90 to allow control unit 90 to adjust flow through the respective flowpaths to achieve a desired flowrate. Control unit 90 may use the feedback, for example, to increase or decrease the flowrates through dialysis fluid circuit 50 and/or urea circuit 60 to increase or decrease urea diffusion and/or to cause turbulent flow through urea separation unit 20. In another embodiment, one or more of the sensors 56a, 56b, 66a, 66b may be a pH sensor or another sensor that monitors a physical property of the fluids flowing through the respective flowpaths. Control unit 90 may use the feedback, for example, to add acidic or basic fluid to the secondary fluid to achieve a desired pH through urea circuit 60.

In the illustrated embodiment, dialysis fluid circuit 50 includes a first adsorption device 58 that removes toxins other than urea from the used dialysis fluid flowing through used dialysis fluid flowpath 50a. First adsorption device 58 may remove, for example, creatinine, uric acid, proteins, and phosphate from the used dialysis fluid flowing through dialysis fluid circuit 50. In an embodiment, first adsorption device 58 includes, for example, conventional sorbents such as activated carbon, silicates, polymers, zeolites, and ion exchange resins. However, such conventional sorbents may not provide the requisite adsorption of urea under the pH and temperature conditions normally found with dialysate solutions (for example, in peritoneal dialysis or hemodialysis therapies). In certain non-limiting embodiments, methods and apparatuses according to the present disclosure use the urea permselective membrane 26 to provide the requisite separation of urea from the dialysis fluid circuit before the urea is cleansed from the system.

In the illustrated embodiment, urea circuit 60 includes a second adsorption device 68 that removes potentially toxic substances created as urea is cleansed from system 10 by urea removal unit 40. For example, if urea is enzymatically oxidized to ammonia via a urease enzyme, ammonium is a product. Ammonium toxicity is high, so second adsorption device 68 ensures that the ammonium does not diffuse through membrane 26 to dialysis fluid circuit 50. Other potentially toxic species that may be generated by urea removal unit 40, and which may require removal by second adsorption device 68 include, for example, traces of gluconate generated during urea electrooxidation or heavy metals generated by an electrocatalyst.

In an embodiment, urea removal unit 40 can be included in a same housing with urea separation unit 20. In another embodiment, urea removal unit 40 can be located within urea chamber 24 of urea separation unit 20.

Figure 2:
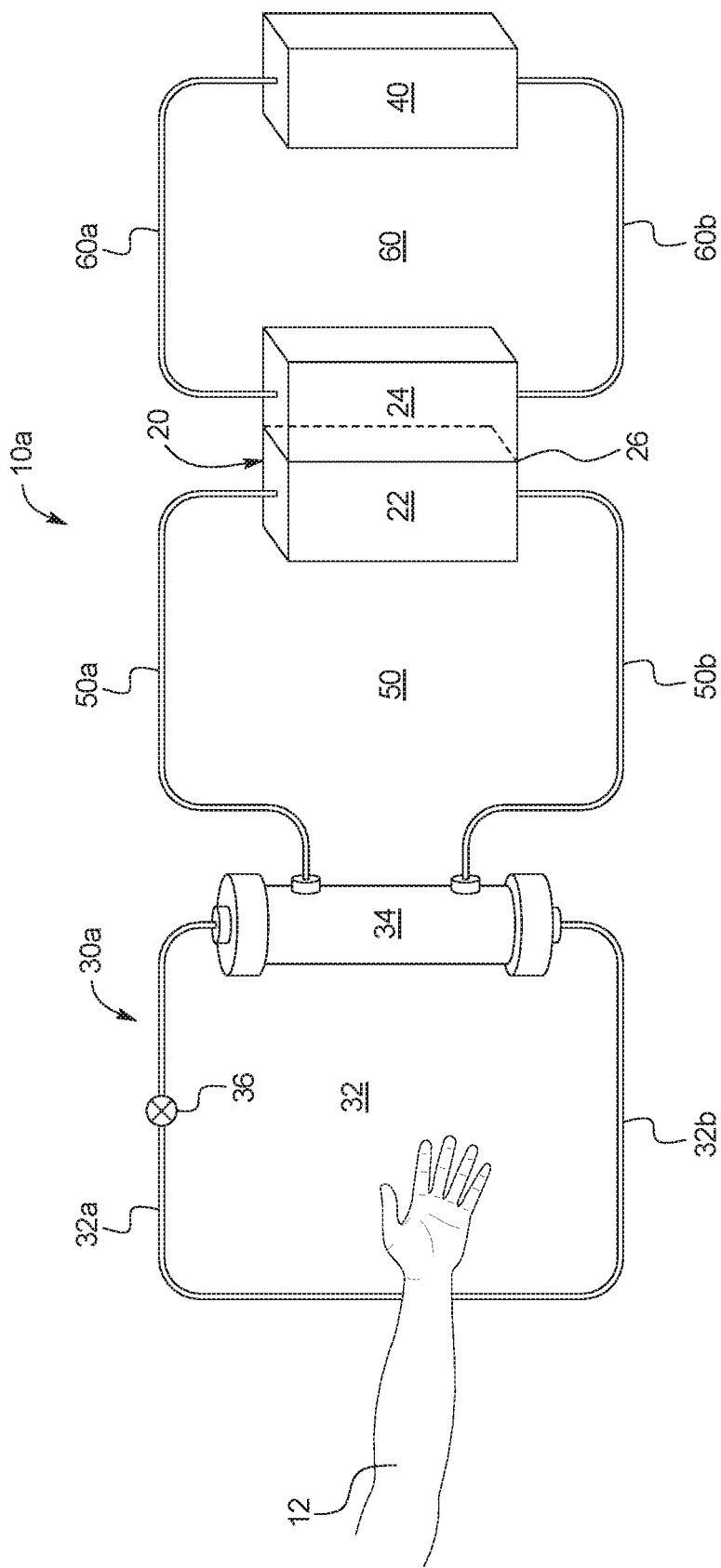
FIG. 2 illustrates an example embodiment of another regenerative dialysis fluid system according to the present disclosure.
Figure 3:
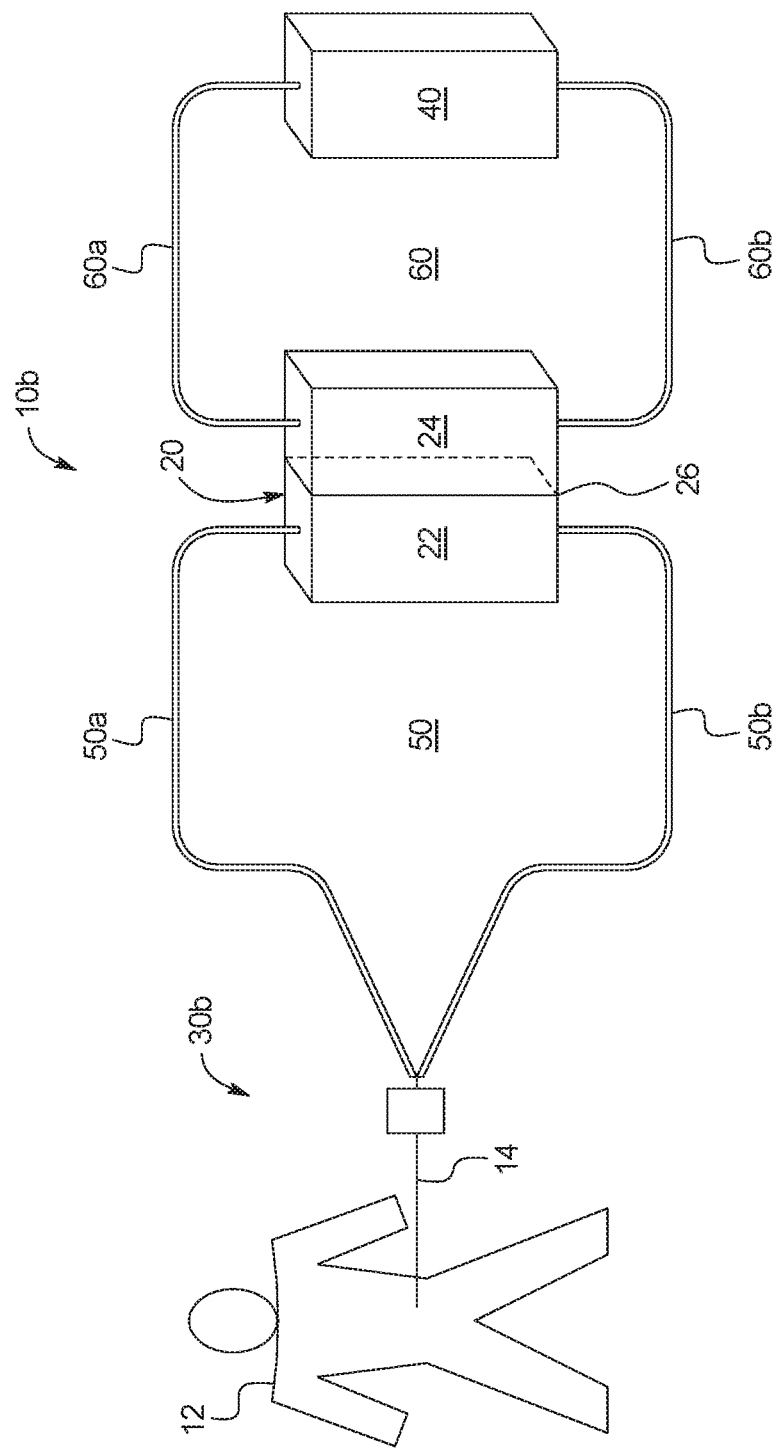
FIG. 3 illustrates an example embodiment of a third regenerative dialysis fluid system according to the present disclosure.
Figure 4:
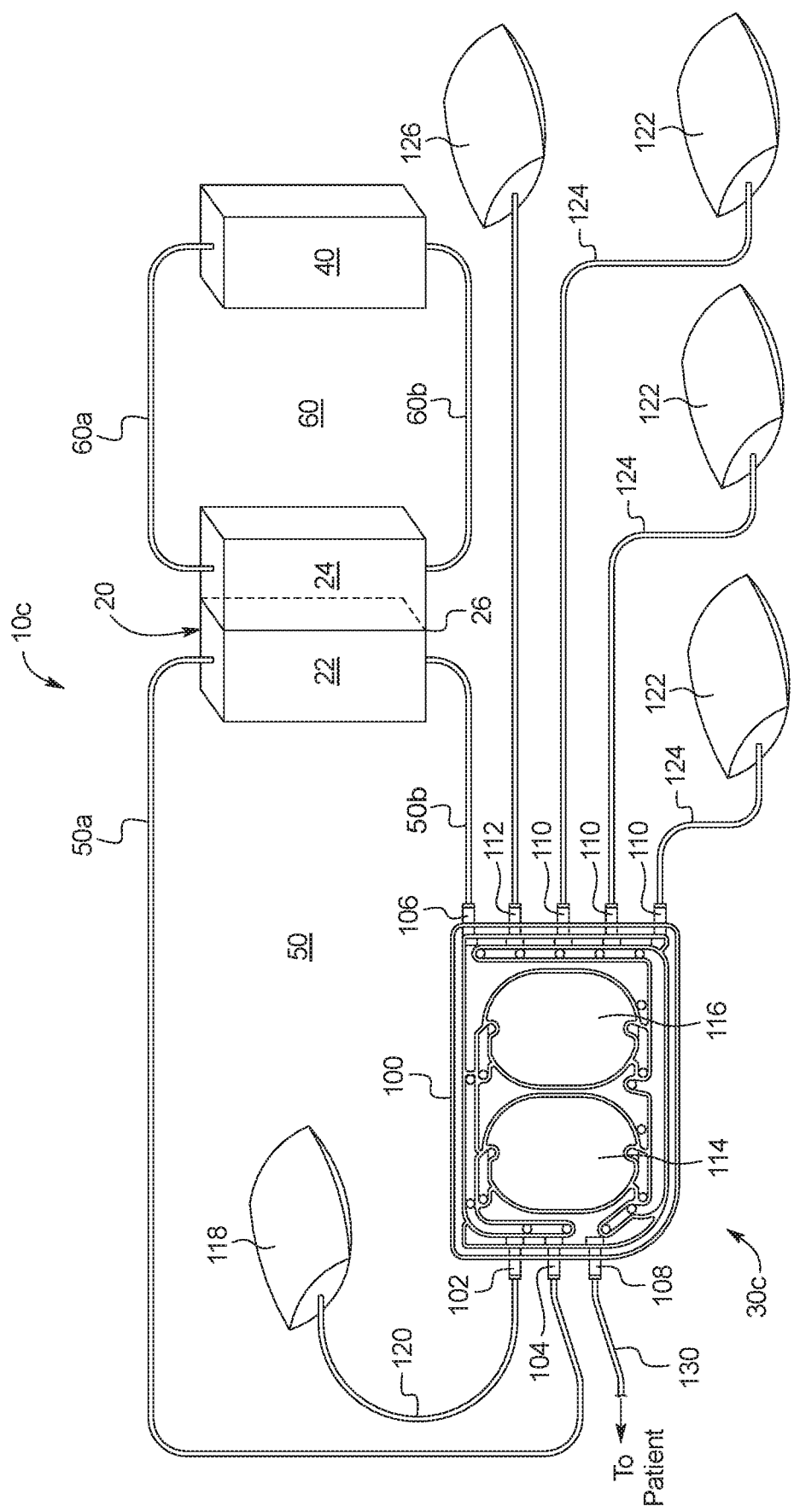
FIG. 4 illustrates an example embodiment of a fourth regenerative dialysis fluid system according to the present disclosure.

In alternative embodiments, dialysis unit 30 may include a blood unit and/or a peritoneal dialysis unit. FIG. 2 illustrates an embodiment of a system 10a in which unit 30 is a blood unit 30a. FIGS. 3 and 4 illustrate embodiments of systems 10b, 10c in which unit 30 is a peritoneal dialysis unit 30b, 30c.

FIG. 2 illustrates an embodiment of a system 10a in which dialysis unit 30 is a blood unit 30a. Blood unit 30a may be, for example, a hemodialyzer used for hemodialysis or hemodiafiltration or a hemofilter.

As illustrated, blood unit 30a includes a blood circuit 32 including an arterial line 32a, a venous line 32b, a blood filter 34 and a blood pump 36. Blood pump 36 pumps blood from and returns blood to a patient 12. Blood is pumped from patient 12 via arterial line 32a, and is returned to the patient via a venous line 32b. Arterial line 32a may include an arterial line connector that connects to an arterial needle, which is in blood draw flow communication with patient 12. Venous line 16 may include a venous line connector that connects to a venous needle, which is in blood return flow communication with patient 12.

In an embodiment, arterial line 32a and/or venous line 32b can include a drip chamber, which may be vented to atmosphere via a hydrophobic membrane for the priming of blood circuit 32. The drip chamber may be used to remove air bubbles from the blood before the blood is returned to the patient. Blood circuit 32 may also include sensors, for example, one or more pressure sensor, an air detector, and/or flow rate sensors that provide feedback to control unit 90 so that control unit 90 may control blood pump 36 to achieve a desired flow rate. Pressure sensors may feed to control unit 90 to determine when flow through arterial line 32a and/or venous line 32b is obstructed and/or when there has been an access disconnection with the patient 12.

In use, blood is pumped from the patient to blood filter 34, which filters waste fluid from the blood. With hemodialysis, for example, dialysis fluid is pumped along the outside of membranes of blood filter 34, while blood is pumped through the insides of the membranes. Waste fluid from the blood is filtered across the membranes into the dialysis fluid.

In system 10a, dialysis fluid circuit 50 provides dialysis fluid to the outside of the membranes of blood filter 34. The dialysis fluid entering blood filter 34 via dialysis fluid circuit 50 should be free of urea, while the dialysis fluid exiting blood filter 34 via dialysis fluid circuit 50 will contain urea along with other waste fluid removed from the patient's blood. By cleansing the dialysis fluid of urea and other waste fluid, system 10a may recycle the dialysis fluid exiting blood filter 34 via dialysis fluid circuit 50 and reduce the total volume of dialysis fluid used for a therapy.

The pumps 52a, 52b, 62a, 62b, valves 54a, 54b, 64a, 64b, 80, 84, 94, 96, 99 sensors 56a, 56b, 66a, 66b, absorption devices 58, 68 and fluid bags 82, 86, 92 have been omitted from FIG. 2 for simplicity, but it should be understood that all of these elements may be included in system 10b and operated by control unit 90 as described above. Additionally, arterial line 32a and venous line 32b may include one or more pumps, valves and/or sensors that are controlled by control unit 90 to achieve desired flowrates and monitor the blood flowing therethrough.

FIG. 3 illustrates an embodiment of a system 10b in which dialysis unit 30 is a peritoneal dialysis unit 30b. Peritoneal dialysis unit 30b may include a catheter 14, as illustrated. In other embodiments, peritoneal dialysis unit 30b may include, for example, a peritoneal dialysis cycler that operates to perform, for example, continuous ambulatory peritoneal dialysis ("CAPD"), automated peritoneal dialysis ("APD"), or a batch type peritoneal dialysis.

As illustrated, with peritoneal dialysis unit 30b, dialysis fluid circuit 50 may be placed in direct fluid communication with the patient 12 by connecting the dialysis fluid circuit 50 to the patient's peritoneum via a catheter 14. Dialysis fluid circuit 50 pulls used dialysis fluid from the patient's peritoneum via used dialysis fluid flowpath 50a of dialysis fluid circuit 50. Clean regenerated dialysis fluid is returned to the patient's peritoneum via regenerated dialysis fluid flowpath 50b.

The pumps 52a, 52b, 62a, 62b, valves 54a, 54b, 64a, 64b, 80, 84, 94, 96, 99 sensors 56a, 56b, 66a, 66b, absorption devices 58, 68 and fluid bags 82, 86, 92 have been omitted from FIG. 3 for simplicity, but it should be understood that all of these elements may be included in system 10b and operated by control unit 90 as described above.

FIG. 4 illustrates an embodiment of a system 10c in which dialysis unit 30 is a batch peritoneal dialysis unit or cycler 30c that operates a disposable cassette 100. One suitable PD cycler is marketed under the tradename Amia®, provided by the assignee of the present disclosure.

In the illustrated embodiment, disposable cassette 100 includes a heater bag port 102, a dialysis fluid regeneration outlet port 104, a dialysis fluid regeneration inlet port 106, a patient port 108, a plurality of solution bag ports 110, and an ultrafiltration bag port 112. Disposable cassette 100 also includes a first pumping chamber 114 and a second pumping chamber 116, which are configured to be actuated by respective pump actuators controlled by control unit 90 to pump fluid through the fluid lines of and attached to the cassette. As illustrated, a heater bag 118 is fluidly connected to heater bag port 102 via a heater bag line 120, a plurality of solution bags 122 are fluidly connected to the plurality of solution bag ports 110 via solution bag lines 124, an ultrafiltration bag 126 is fluidly connected to ultrafiltration bag port 112 via an ultrafiltration bag line 128, and a patient may be fluidly connected to patient port 108 via a patient line 130. Dialysis fluid regeneration outlet port 104 is fluidly connected to an inlet of used dialysis fluid chamber 22 via used dialysis fluid flowpath 50a, and dialysis fluid regeneration inlet port 106 is fluidly connected to an outlet of used dialysis fluid chamber 22 via regenerated dialysis fluid flowpath 50b.

In use, dialysis fluid from one of the plurality of solution bags 122 may be pumped by at least one of first pumping chamber 114 and second pumping chamber 116 to heater bag 118, where the dialysis fluid may be heated to the appropriate temperature (e.g., 37° C.) to be delivered to the patient. Once heated, the dialysis fluid may be pumped from heater bag 118 to the patient via patient line 130. The dialysis fluid may then be allowed to dwell within the patient for a period of time to remove toxins and ultrafiltrate from the patient. The used dialysis fluid including ultrafiltrate may then be removed from the patient after the dwell period via patient line 130. The used dialysis fluid may be pumped back to the solution bag 122 that it came from, and any excess ultrafiltrate may be pumped to ultrafiltration bag 126. The process may then be repeated with fresh dialysis fluid from another of the plurality of solution bags 122 filled with fresh dialysis fluid.

After treatment using multiple solution bags is completed, each of the plurality of solution bags 122 is at that time filled with used dialysis fluid that requires regeneration for reuse by system 10c. Dialysis fluid from the first of the plurality of solution bags 122 may be pumped through cassette 100, by at least one of first pumping chamber 114 and second pumping chamber 116, through dialysis fluid regeneration outlet port 104 to used dialysis fluid chamber 22 via used dialysis fluid flowpath 50a. The used dialysis fluid may be regenerated as described above by filtering the urea through membrane 26 into urea circuit 60, and by cleansing the other toxins via an adsorption device 58. The regenerated dialysis fluid may then be recirculated via pumping chambers 114 and/or 116 back through regenerated dialysis fluid flowpath 50b, dialysis fluid regeneration inlet port 106, cassette 100 and solution bag port 110 to the solution bag 122 from which it originated. In an embodiment, the dialysis fluid is pumped through dialysis fluid circuit 50 for a number of passes known to fully or acceptably regenerate the dialysis fluid before being pumped back to the solution bag 122 from which it originated. The number of passes may be determined empirically, for example.

The process may then be repeated for each of the other solution bags 122, so that each of the solution bags 122 contains useable regenerated dialysis fluid for a subsequent treatment. It is therefore expressly contemplated to enable the patient to perform multiple PD cycles overnight and to regenerate the dialysis fluid during the day to provide multiple fluid bags 122 for the next evening. Control unit 90 may be programmed to perform at least a portion of the regeneration in the morning so that at least one bag 122 is regenerated by noon for a mid-day exchange.

It is believed that isolating different bags 122 in the above-described manner may allow one of the bags 122 to be a "last bag", meaning that it is used for the last night fill that remains with the patient until the next evening or until a mid-day exchange. The last fill bag 122 typically includes a higher dextrose level than the other bags. If the patient returns for a mid-day exchange or the next evening, the first step is to drain the patient into the last fill bag 122.

Urea circuit 60 and urea removal unit 40 may be operated as described herein for system 10c. In an embodiment, first pumping chamber 114 and second pumping chamber 116 may be used to pump fluid through dialysis fluid circuit 50, and a pump 62 may be placed in fluid communication with urea circuit 60 to pump the secondary fluid through urea circuit 60. In an embodiment, one of first pumping chamber 114 and second pumping chamber 116 may be used to pump used dialysis fluid through used dialysis fluid flowpath 50a, and the other of first pumping chamber 114 and second pumping chamber 116 may be used to pump regenerated dialysis fluid through regenerated dialysis fluid flowpath 50b. The pump 62 in urea circuit 60 may be included as part of cassette 100, or may be a separate pump. Any of the other pumps 52a, 52b, 62a, 62b, valves 54a, 54b, 64a, 64b, 80, 84, 94, 96, 99, sensors 56a, 56b, 66a, 66b, absorption devices 58, 68 and fluid bags 82, 86, 92 described herein may also be included in system 10c and operated by control unit 90 as described above. The pumps 52a, 52b, 62a, 62b, valves 54a, 54b, 64a, 64b, 80, 84, 94, 96, 99 sensors 56a, 56b, 66a, 66b, absorption devices 58, 68 and fluid bags 82, 86, 92 have been omitted from FIG. 4 for simplicity, but it should be understood that all of these elements may be included in system 10c and operated by control unit 90 as described above.

In an embodiment, ultrafiltration bag 126 may be replaced after each treatment to remove the excess ultrafiltrate from system 10c. In another embodiment, ultrafiltration bag 126 may be a large bag (e.g., a 6 to 12 liter bag), which may store a week's worth of ultrafiltrate before being replaced.

In alternative embodiments, urea removal unit 40 may be, for example, a chemical adsorption unit, an electrooxidation unit and/or an enzymatic oxidation unit. Each of these embodiments is discussed in more detail below.

Figure 5:
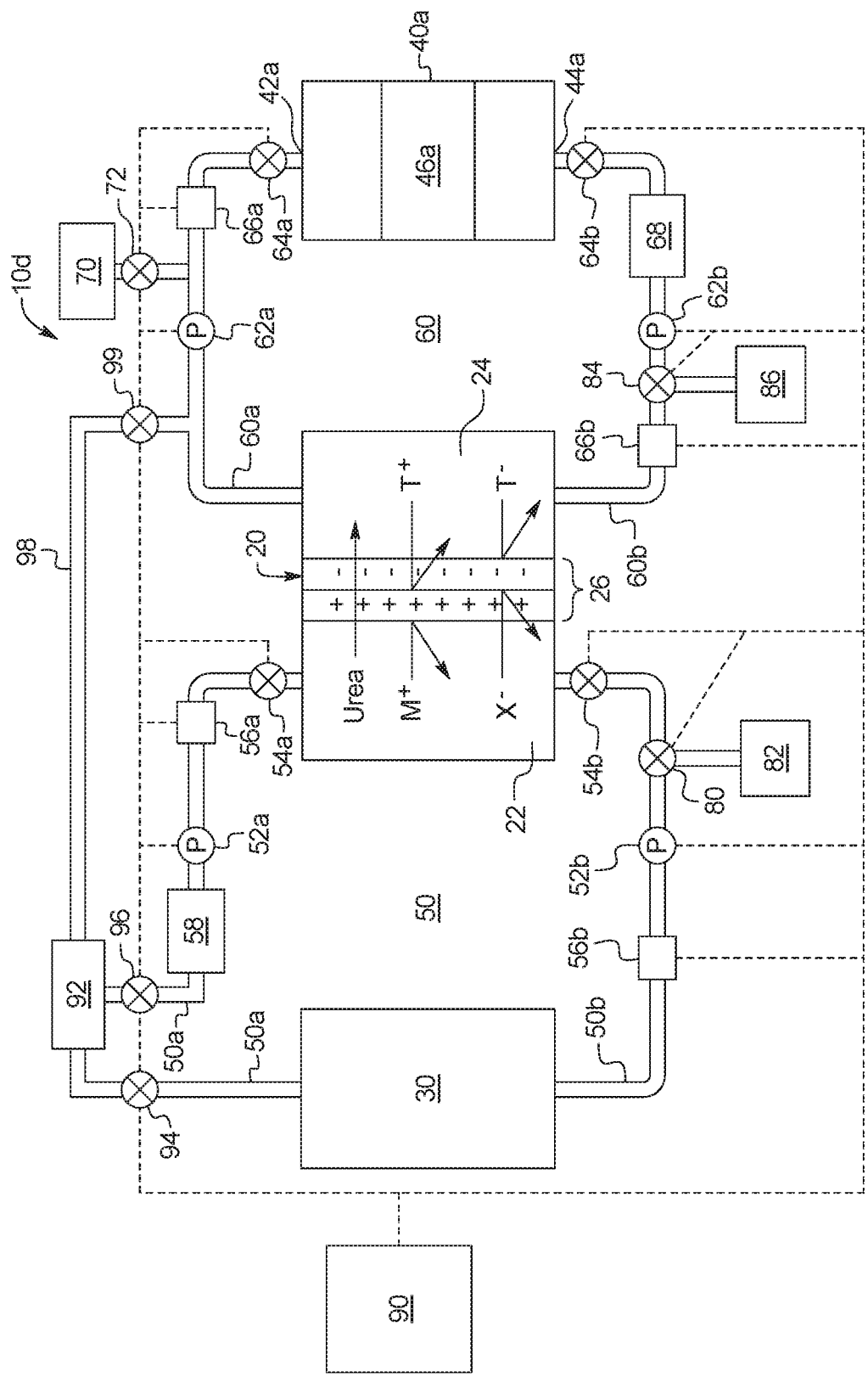
FIG. 5 illustrates an example embodiment of a fifth regenerative dialysis fluid system according to the present disclosure.

FIG. 5 illustrates an embodiment of a system 10d in which urea removal unit 40 is a urea adsorption unit 40a. Urea adsorption unit 40a includes an inlet 42a for the entry of secondary fluid having urea, an outlet 44a for the removal of cleansed secondary fluid, and an adsorbent 46a that binds to urea, removing urea from the secondary fluid flowing through urea circuit 60 as the secondary fluid containing urea flows through urea adsorption unit 40a between first flowpath 60a and second flowpath 60b of urea circuit 60. The adsorbent 46a may include, for example, a polymer containing a carbonyl group such as oxidized cellulose or oxidized starch, cyclodextrin, ninhydrin or another material that binds to urea. In an embodiment, a carbonyl group able to bind to urea includes oxidized polysaccharides (cellulose, starch, cyclodextrins, etc.). In another embodiment, adsorbent 46a may include, for example, a urea binding substance in a solution or a solid support such as, for example, glyoxal, orthophtalaldehyde, ninhydrin or the like. In another embodiment, a solid sorbent for adsorbent 46a may include, for example, activated carbon, copper-chitosan composites, polyethylene oxide containing polymers, molecularly imprinted polymers or the like. In an embodiment, adsorbent 46a may be reusable or replaceable within system 10d.

It has been determined that urea adsorption unit 40a more effectively absorbs urea when the pH of the secondary fluid containing urea is acidic, so it may be preferable in one embodiment to drop the pH of the secondary fluid flowing through urea circuit 60 in system 10d. System 10d may therefore include a source of acidic solution 70 that branches off of urea circuit 60. Sensor 66a and/or sensor 66b may include a pH sensor that is configured to detect the pH of the secondary fluid flowing through first flowpath 60a and second flowpath 60b, respectively. Control unit 90 may continuously or intermittently receive a pH reading from sensor 66*a* and/or sensor 66*b* and control valve 72 to precisely control the pH of the secondary fluid flowing through urea circuit 60. In an embodiment, system 10*d* may also include a source of basic solution (not illustrated) that is in fluid communication with urea circuit 60, and control unit 90 may control a pump to pump the basic solution into urea circuit 60 if the pH of the secondary fluid becomes too low.

Although it may be desirable to lower the pH of the secondary fluid in urea circuit 60, the dialysis fluid flowing through dialysis fluid circuit 50 should be kept at a neutral pH and/or a physiological pH. Membrane 26 ensures that the dialysis fluid in dialysis fluid circuit 50 remains neutral, because the positive charge in membrane 26 repels positive ions (e.g., H+) from the lower pH secondary fluid in urea circuit 60, allowing the dialysis fluid in dialysis fluid circuit 50 to remain neutral even when the secondary fluid in urea circuit 60 has an acidic pH.

In an embodiment, second adsorption device 68 may be eliminated from system 10*d* if urea adsorption unit 40*a* does not create toxic leachables that could potentially seep into dialysis fluid circuit 50. Optionally, a second adsorption device 68 may be included in system 10*d* and include, for example, activated carbon to absorb a small amount of urea not absorbed by urea adsorption unit 40*a*, as well as other contaminants that may be present in urea circuit 60.

The pumps 52*a*, 52*b*, 62*a*, 62*b*, valves 54*a*, 54*b*, 64*a*, 64*b*, 80, 84, 94, 96, 99, sensors 56*a*, 56*b*, 66*a*, 66*b* and fluid bags 82, 86, 92 may be operated by control unit 90 as illustrated and described herein.

Figure 6:
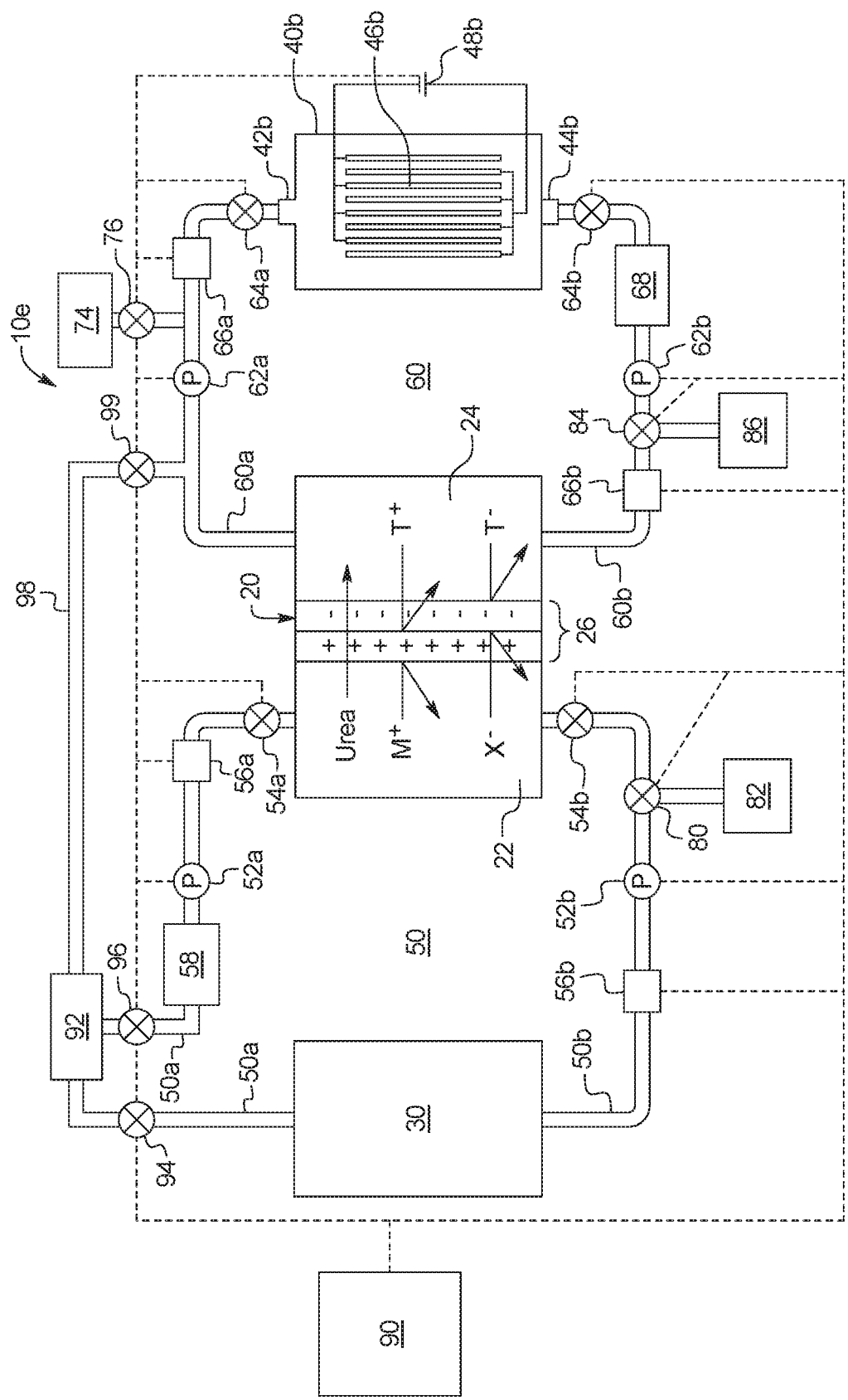
FIG. 6 illustrates an example embodiment of a sixth regenerative dialysis fluid system according to the present disclosure.

FIG. 6 illustrates an embodiment of a system 10*e*, in which urea removal unit 40 is an electrooxidation unit 40*b*, which is configured to oxidize urea into, for example, nitrogen, hydrogen, carbon dioxide and other organic byproducts, so that secondary fluid containing urea may be cleansed of the urea. In the illustrated embodiment, electrooxidation unit 40*b* includes an inlet 42*b* for the entry of secondary fluid having urea, an outlet 44*b* for the removal of cleansed secondary fluid, and one or more sets of electrodes 46*b* with electrocatalytic surfaces for the decomposition of urea via electrooxidation. Each set of electrodes 46*b* may include an anode and a cathode. In an embodiment, the anodes comprise a transition metal and/or mixtures thereof and/or alloys thereof. The transition metal may be selected from the group consisting of cobalt, copper, iron, nickel, platinum, palladium, iridium, ruthenium, and rhodium. In an embodiment, the cathode includes platinum and the anode includes nickel, nickel oxide, nickel hydroxide or nickel oxide hydroxide (NiOOH). The urea decomposition unit 40*b* may also include an alkaline polymeric gel.

Electrooxidation unit 40*b* may further include a power source 48*b* to provide the electrodes 46*b* with an electrical charge. The power source 48*b* provides the electrodes 46*b* with an electrical charge to activate the electrocatalytic surfaces of the electrodes. The voltage difference applied across the electrodes (e.g. cathode and anode) may be sufficient to produce nitrogen gas, carbon dioxide gas, and water.

In use, secondary fluid containing urea passes into electrooxidation unit 40*b* via inlet 42*b*. The power source 48*b* then charges the electrodes 46*b*, which create an electrical current sufficient to oxidize the urea in the secondary fluid into, for example, nitrogen, hydrogen, carbon dioxide and/or other organic byproducts. The secondary fluid then exits urea decomposition unit 40*b* via outlet 44*b* as secondary fluid without urea or a substantially reduced amount of urea (e.g., about 10%, 20%, 30%, 40%, 50%, 60%, 70%, 80%, or 90% of the amount of urea prior to entering the electrooxidation unit 40*b*).

It has been determined that electrooxidation unit 40*b* more effectively oxidizes urea when the pH of the secondary fluid containing urea is basic, so it may be preferable in one embodiment to raise the pH of the secondary fluid flowing through urea circuit 60 in system 10*e*. System 10*e* may therefore include a source of basic solution 74 that branches off of urea circuit 60. Sensor 66*a* and/or sensor 66*b* may include a pH sensor that is configured to detect the pH of the secondary fluid flowing through first flowpath 60*a* and second flowpath 60*b*, respectively. Control unit 90 may continuously or intermittently receive a pH reading from sensor 66*a* and/or sensor 66*b* and control valve 76 to precisely control the pH of the secondary fluid flowing through urea circuit 60. In an embodiment, system 10*e* may also include a source of acidic solution (not illustrated) that is in fluid communication with urea circuit 60, while control unit 90 is programmed to control a pump to pump the acidic solution into urea circuit 60 if the pH of the secondary fluid becomes too high.

Although it may be desirable to raise the pH of the secondary fluid in urea circuit 60, the dialysis fluid flowing through dialysis fluid circuit 50 is kept at a neutral pH in one embodiment. Membrane 26 ensures that the dialysis fluid in dialysis fluid circuit 50 remains neutral, because the negative charge in membrane 26 repels negative ions (e.g., OH—) from the higher pH secondary fluid in urea circuit 60, allowing the dialysis fluid in dialysis fluid circuit 50 to remain neutral even when the secondary fluid in urea circuit 60 has a basic pH. According to certain non-limiting embodiments, urea permselective membrane 26 is charged on the side facing the dialysis fluid circuit 50 (left in FIG. 6) with a positive charge, and charged on the side facing the urea circuit 60 (right in FIG. 6) with a negative charge.

Electrooxidation may produce, for example, traces of gluconate, chlorinated species, reactive oxygen species, and other urea oxidation byproducts. A second adsorption device 68 may be provided and configured to remove the byproducts from the secondary fluid pumped through second flowpath 60*b* of urea circuit 60. Electrooxidation may also produce traces of metal ions from transitions metals, and traces of transition metal ions may also leach from the electrodes even when the electrodes are not activated. The metal ions, however, are prevented from crossing into dialysis fluid circuit 60 due to the positive and negative charges of membrane 26, as demonstrated in FIG. 6 by the T+ ions (positive metal ions) and the T− ions (negative metal ions). In an embodiment, second adsorption device 68 may include an adsorbent to absorb at least a portion of the metal ions created during the electrooxidation process.

The pumps 52*a*, 52*b*, 62*a*, 62*b*, valves 54*a*, 54*b*, 64*a*, 64*b*, 80, 84, 94, 96, 99, sensors 56*a*, 56*b*, 66*a*, 66*b* and fluid bags 82, 86, 92 may be operated by control unit 90 as illustrated and described herein.

Figure 7:
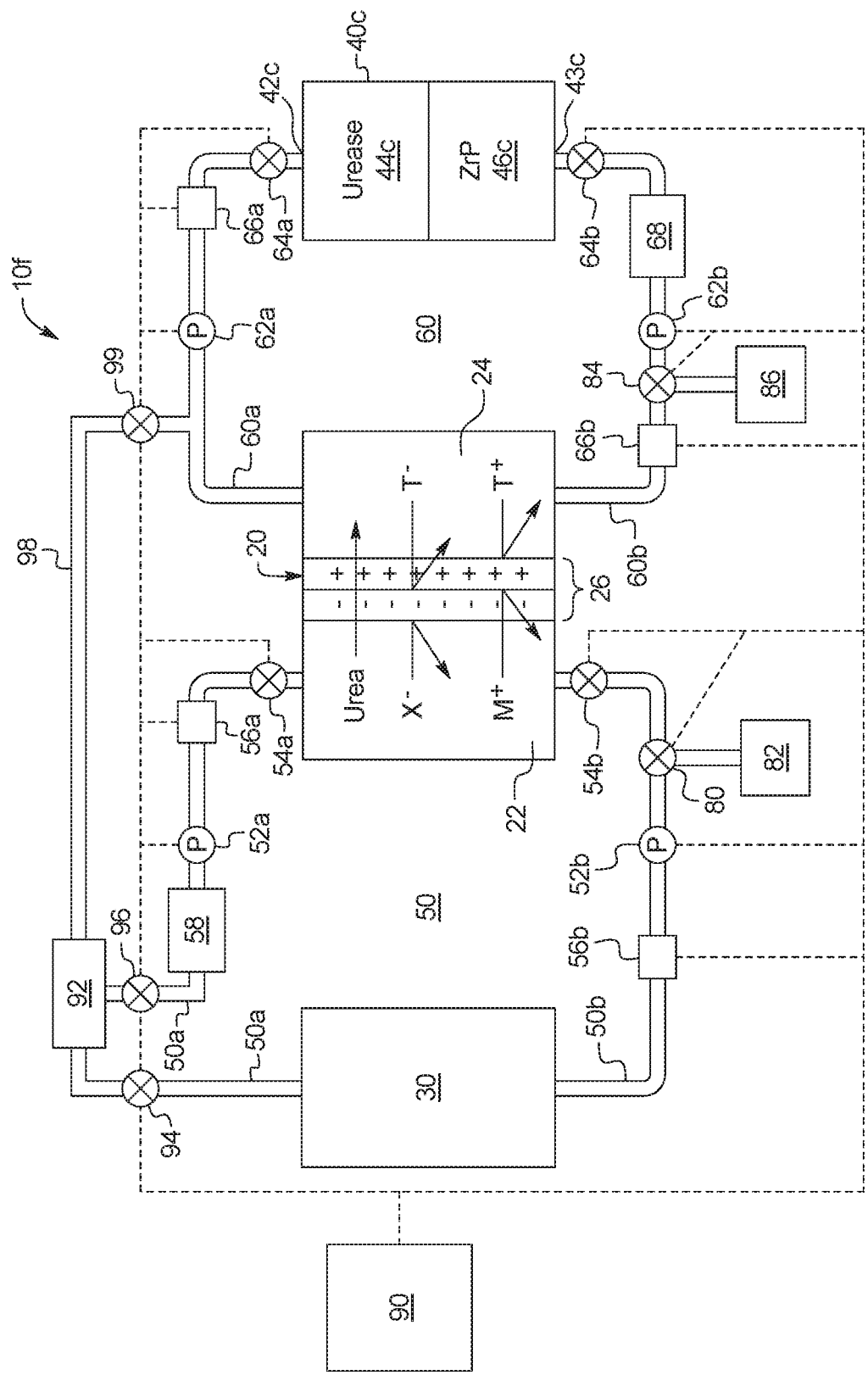
FIG. 7 illustrates an example embodiment of a seventh regenerative dialysis fluid system according to the present disclosure.

FIG. 7 illustrates an embodiment of a system 10*f* in which urea removal unit 40 is an enzymatic oxidation unit 40*c*. Enzymatic oxidation unit 40*c* includes an inlet 42*c* for the entry of secondary fluid having urea, an outlet 43*c* for the removal of cleansed secondary fluid, a urease compartment 44*c* that converts urea into ammonium, and a zirconium phosphate compartment 46*c* that captures the ammonium. In an embodiment, urease unit includes immobilized urease.

In use, as secondary fluid containing urea enters urease compartment 44*c*, the urea in the secondary fluid is converted to ammonium as it contacts the urease in urease compartment 44c. The ammonium is then be removed from the secondary fluid by zirconium phosphate compartment 46c. According to certain non-limiting embodiments, the urea permselective membrane 26 is charged on the side facing the dialysis fluid circuit 50 (left in FIG. 7) with a negative charge, and charged on the side facing the urea circuit 60 (right in FIG. 7) with a positive charge. Even if all of the ammonium is not captured by zirconium phosphate compartment 46c, the ammonium may not pass through membrane 26 into dialysis fluid circuit 50 because ammonium is positively charged and is rejected by the positive charge of membrane 26.

Second adsorption device 68 may be eliminated from system 10f because zirconium phosphate compartment 46c captures the ammonium created by urease compartment 44c. Optionally, second adsorption device 68 may be included in system 10f and may include, for example, activated carbon to absorb a small amount of urea not converted to ammonium by urease compartment 44c, as well as other contaminants that may be present in urea circuit 60. Alternatively, enzymatic oxidation unit 40c may include urease compartment 44c, and second adsorption device 68 may include zirconium phosphate compartment 46c. In an embodiment, zirconium phosphate compartment 46c may be regenerated by electrolytes for reuse. In another embodiment, zirconium phosphate compartment 46c and/or urease compartment 44c may be provided in a replaceable cartridge which may be replaced to allow system 10f to be reused.

The pumps 52a, 52b, 62a, 62b, valves 54a, 54b, 64a, 64b, 80, 84, 94, 96, 99, sensors 56a, 56b, 66a, 66b and fluid bags 82, 86, 92 may be operated by control unit 90 as illustrated and described herein.

Figure 8:
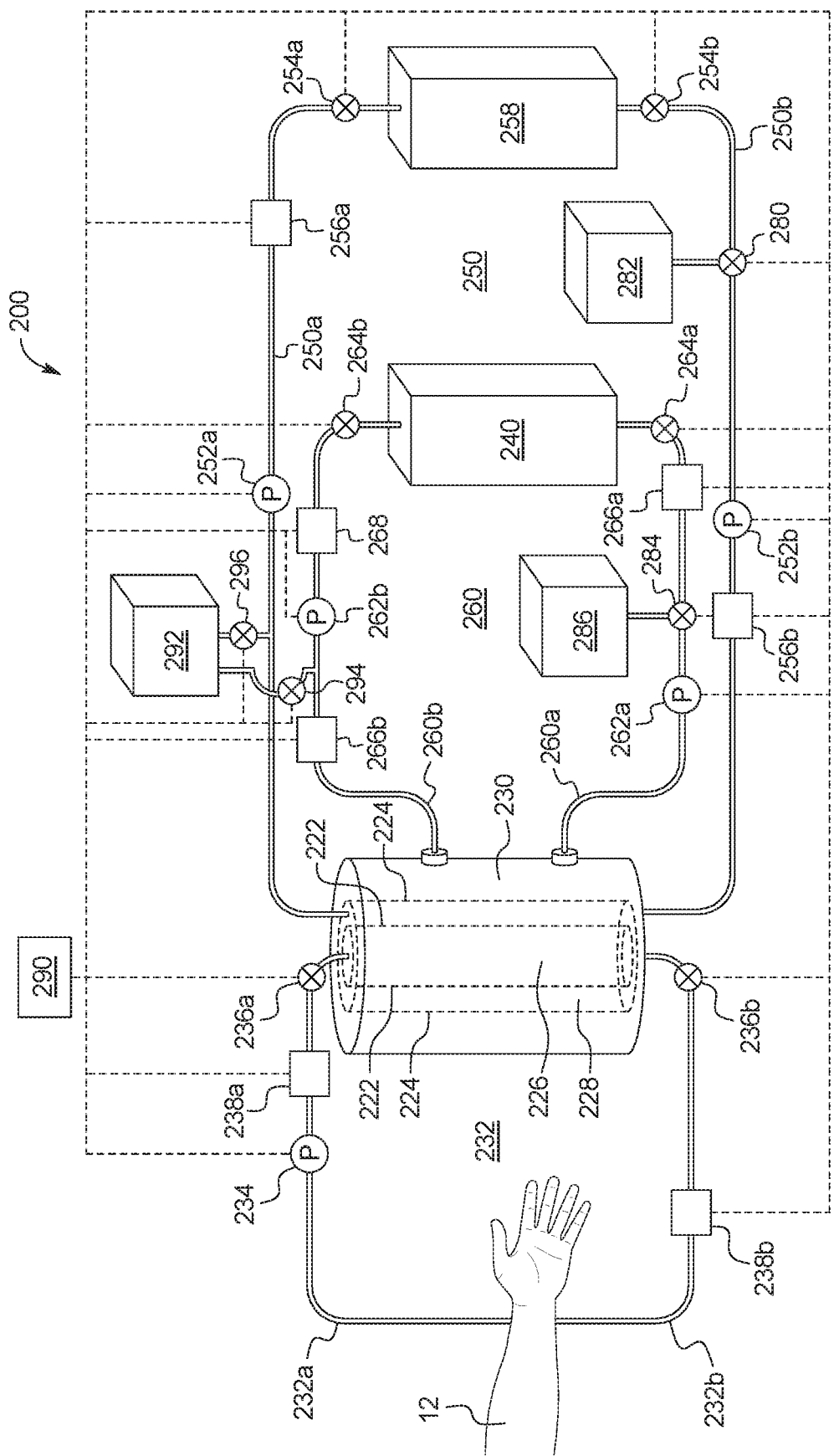
FIG. 8 illustrates an example embodiment of an eighth regenerative dialysis fluid system according to the present disclosure.
Figure 9:
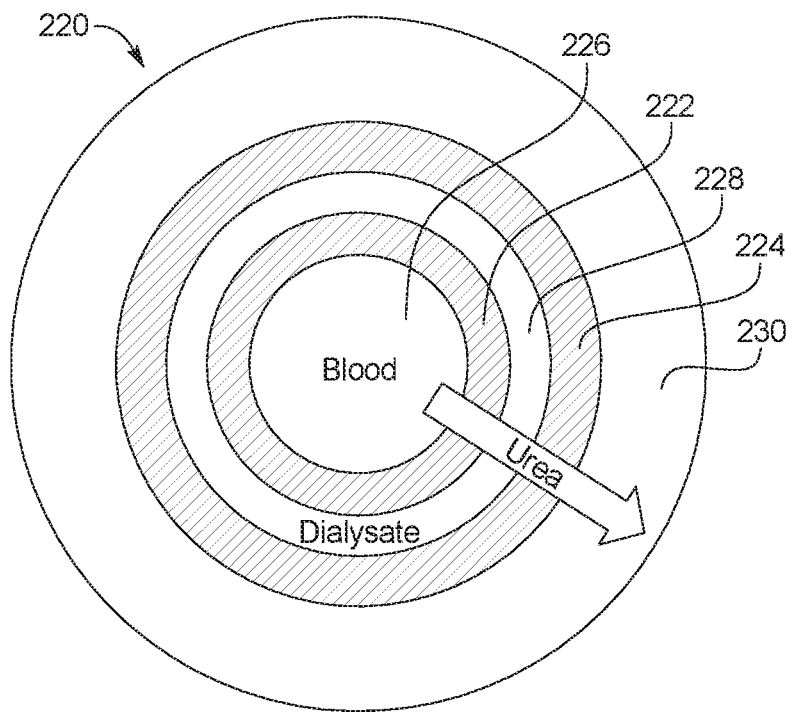
FIG. 9 illustrates the operation of the urea separation unit of FIG. 8.
Figure 10:
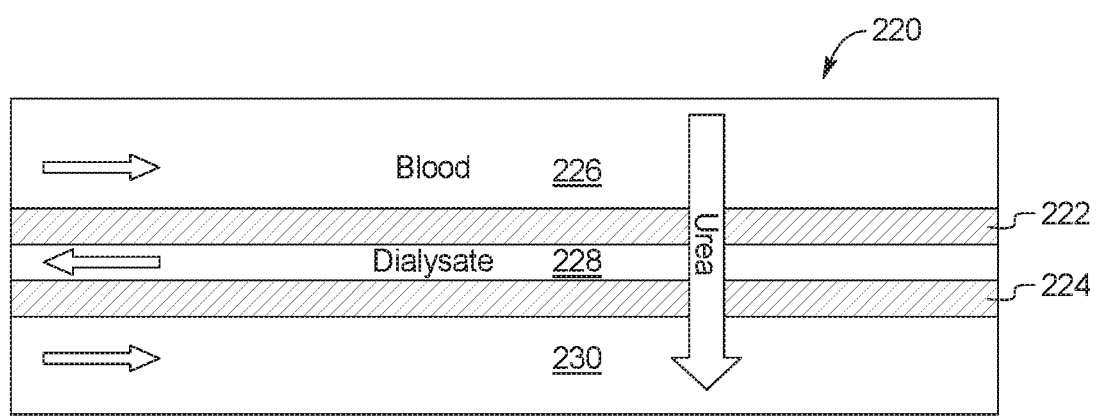
FIG. 10 illustrates the operation of the urea separation unit of FIG. 8.

FIG. 8 illustrates an alternative embodiment of a regenerative dialysis fluid system 200, which includes a urea separation unit 220 that combines the blood filter 34 of FIG. 2 with the urea separation unit 20 of FIGS. 1 to 7. FIGS. 9 and 10 illustrate the operation of urea separation unit 220.

As illustrated, urea separation unit 220 includes one or more waste membrane 222 and one or more charged membrane 224, both of which are illustrated in broken lines in FIG. 8. A blood compartment 226 is formed within waste membrane 222, a dialysis fluid compartment 228 is formed between waste membrane 222 and charged membrane 224, and a urea compartment 230 is formed outside of charged membrane 224. A blood circuit 232 is placed in fluid communication with blood compartment 226, a dialysis fluid circuit 250 is placed in fluid communication with dialysis fluid compartment 228, and a urea circuit 260 is placed in fluid communication with urea circuit 260.

In alternative embodiments, the configurations and/or sizes of the membranes 222 and 224 and compartments 226, 228, 230 can be altered or optimized without departing from the spirit and scope of the present disclosure. For example, waste membrane 222 and blood compartment 226 can be formed by a bundle of hollow fiber membranes or pleated membranes, and/or charged membrane 224 can be formed as a flat sheet. Those of ordinary skill in the art will recognize other suitable configurations that can be used.

As illustrated, system 200 may also include one or more pump 234, 252a, 252b, 262a, 262b and/or a plurality of valves 236a, 236b, 254a, 254b, 264a, 264b, 280, 284, 294, 296 that control fluid flow along the respective flowpaths. Pumps 234, 252a, 252b, 262a, 262b may for example be peristaltic pumps or volume membrane pumps. Valves 236a, 236b, 254a, 254b, 264a, 264b, 280, 284, 294, 296 may for example be variable fluid orifice valves, solenoid valves or other valves known to those of ordinary skill in the art. In the illustrated embodiment, the pumps 234, 252a, 252b, 262a, 262b and valves 236a, 236b, 254a, 254b, 264a, 264b, 280, 284, 294, 296 are electrically connected to control unit 290. Control unit 290 may include one or more processor and memory programmed to control pumps 234, 252a, 252b, 262a, 262b and the valves 236a, 236b, 254a, 254b, 264a, 264b, 294, 296. Control unit 290 may control the pumps 234, 252a, 252b, 262a, 262b and valves 236a, 236b, 254a, 254b, 264a, 264b, 280, 284 to control transmembrane pressure. The flowrates through blood compartment 226, dialysis fluid compartment 228 and urea compartment 230 may also be increased by control unit 290 to facilitate urea diffusion. In an embodiment, the flowrates through blood circuit 232, dialysis fluid circuit 250 and urea circuit 260 are about 400 mL/min. In another embodiment, control unit 290 may be used to adjust flow rates so that the Reynolds number on both sides of membrane 222 and/or membrane 224 reduces any stagnant layer formation at a membrane/fluid interface, which may limit the mass transport of urea across membrane 224 or waste fluid across membrane 222. In an embodiment, control unit 290 may cause a turbulent flow with a high Reynolds number against one or both sides of membrane 222 and/or membrane 224 so that a stagnant layer does not form on membrane 222 and/or membrane 224. In other embodiments, techniques such as using pulsatile flow, a baffle design and/or mechanical vibrations, agitations or perturbations can be used to create turbulence near membrane 222 and/or membrane 224 to minimize flow stagnation and enhance mass transfer across membrane 222 and/or membrane 224. The methods and apparatuses described herein are not limited in this regard.

In an embodiment, any one or more or all of valves 236a, 236b, 254a, 254b, 264a, 264b, 280, 284, 294, 296 may alternatively be solenoid valves that operate with control unit 290 so that they are opened a specified amount of time to achieve appropriate flow distributions through system 200. In a further embodiment, one or more valves 236a, 236b, 254a, 254b, 264a, 264b may be replaced with a balance chamber that operates with its own valves. Each balance chamber may include a first compartment and a second compartment separated by a flexible membrane. When a first inlet solenoid valve opens to allow the first compartment to fill with fluid, the flexible membrane is pushed into the second compartment to expel like fluid from the second compartment through an opened second outlet solenoid valve. When a second inlet solenoid valve opens to allow the second compartment to fill with fluid, the flexible membrane is pushed into the first compartment to expel like fluid from the first compartment through an opened first outlet solenoid valve. Because the volume of the first and second compartments is known, control unit 290 may precisely meter fluid through the flowpaths by toggling the solenoid valves of the balance chamber between the first compartment and the second compartment and control the flow rate by controlling how often the inlet and outlet valves are cycled.

In an embodiment, system 200 includes one or more sensor 238a, 238b, 256a, 256b, 266a, 266b to monitor flow at any desired one or more location within the respective flowpaths of system 200 and provide feedback to control unit 290. In an embodiment, one or more of the sensors 238a, 238b, 256a, 256b, 266a, 266b may be a flowrate sensor, which provides feedback to control unit 290 to allow control unit 290 to adjust flow through the respective flowpaths to achieve a desired flowrate. Control unit 290 may use the feedback, for example, to increase or decrease the flowrates through blood circuit 232, dialysis fluid circuit 250 and/or urea circuit 260 to increase or decrease urea diffusion and/or to cause turbulent flow through urea separation unit 220. In another embodiment, one or more of the sensors 238a, 238b, 256a, 256b, 266a, 266b may be a pH sensor or another sensor that monitors a physical property of the fluids flowing through the respective flowpaths. Control unit 290 may use the feedback, for example, to add acidic or basic fluid to the secondary fluid to achieve a desired pH through urea circuit 260.

As illustrated, blood circuit 232 includes an arterial line 232a, a venous line 232b, and a blood pump 234. Blood pump 234 pulls blood from and returns blood to a patient 12. Blood is pulled from patient 12 via arterial line 232a, and is returned to the patient 12 via venous line 232b. Arterial line 232a may include an arterial line connector that connects to an arterial needle, which is in blood draw flow communication with patient 12. Venous line 232b may include a venous line connector that connects to a venous needle, which is in blood return flow communication with patient 12. In use, blood is pumped from the patient 12 to blood compartment 226, where waste fluid from the blood may be filtered across waste membrane 222 into dialysis fluid compartment 228.

Dialysis fluid circuit 250 includes a used dialysis fluid flowpath 250a and a regenerated dialysis fluid flowpath 250b. At least a portion of the urea in dialysis fluid compartment 228 is pulled across charged membrane 224 as described above with respect to membrane 26. The rest of the dialysis fluid in dialysis fluid compartment 228 is pumped through used dialysis fluid flowpath 250a to adsorption device 258, which removes toxins other than urea from the used dialysis fluid. The adsorption device 258 may remove, for example, creatinine, uric acid and proteins from the used dialysis fluid. In an embodiment, the adsorption device 258 includes, for example, activated carbon, silicates, polymers, zeolites, ion exchange resins, or a capacitive deionization unit. Once the toxins other than urea have been removed from the dialysis fluid by adsorption device 258, the resulting regenerated dialysis fluid may be pumped through regenerated dialysis fluid flowpath 250b back to dialysis fluid compartment 226.

In an embodiment, dialysis fluid circuit 250 may include a valve 280 and a fluid bag 282. In the illustrated embodiment, valve 280 is a three-way valve which allows fluid from fluid bag 282 to be added to dialysis fluid circuit 250. In an embodiment, the fluid in fluid bag 282 may be, for example, dialysis fluid that may be added to dialysis fluid circuit 250 if more fluid is needed in dialysis fluid circuit 250 due to the loss of fluid through membrane 224. In another embodiment, the fluid in fluid bag 282 may be used to raise or lower the pH of dialysis fluid flowing through dialysis fluid circuit 250 or to add electrolytes to the dialysis fluid flowing through dialysis fluid circuit 250. Fluid bag may also be used to drain fluid from dialysis fluid circuit 250 if necessary. In an embodiment, multiple valves 280 and fluid bags 282 may be fluidly connected to dialysis fluid circuit 50 at used dialysis fluid flowpath 250a and/or regenerated dialysis fluid flowpath 250b.

Urea circuit 260 includes a first flowpath 260a and a second flowpath 260b. Secondary fluid containing urea removed from dialysis fluid compartment 228 through charged membrane 224 into urea compartment 230 is pumped through first flowpath 260a to urea removal unit 240, which may include any of the devices described above with respect to urea removal unit 40 or any other urea removal unit. Once at least a portion of the urea has been removed from the secondary fluid containing urea, the secondary fluid may be pumped through second flowpath 260b back to urea chamber 230. Optionally, urea circuit 260 may include an adsorption device 268 that removes potentially toxic substances generated by urea removal unit 240, as described above with respect to second adsorption device 68.

In an embodiment, urea circuit 260 may include a valve 284 and a fluid bag 286. In the illustrated embodiment, valve 284 is a three-way valve which allows excess fluid to be drained from urea circuit 260 into fluid bag 286. In an embodiment, fluid bag 286 may include secondary fluid, and valve 284 may allow secondary fluid from fluid bag 286 to be added to urea circuit 260. In another embodiment, the fluid in fluid bag 286 may be used to raise or lower the pH of secondary fluid flowing through urea circuit 260 or to add electrolytes to the secondary fluid flowing through urea circuit 260. In an embodiment, multiple valves 284 and fluid bags 286 may be fluidly connected to urea circuit 260 at first flowpath 260a and/or second flowpath 260b.

In an embodiment, dialysis fluid circuit 250 and or urea circuit 260 can initially be filled with dialysis fluid from dialysis fluid source 292. In the illustrated embodiment, dialysis fluid from dialysis fluid source can be added to dialysis fluid circuit 250 by opening valve 296, and dialysis fluid can be added to urea circuit 260 by opening valve 294. In an embodiment, about six liters of dialysis fluid can initially be pumped into dialysis fluid circuit 250, and about one liter of dialysis fluid can initially be pumped into urea circuit 250. Urea circuit can also be filled initially with other secondary fluid as described above.

EXPERIMENTAL EXAMPLES

Figure 11:
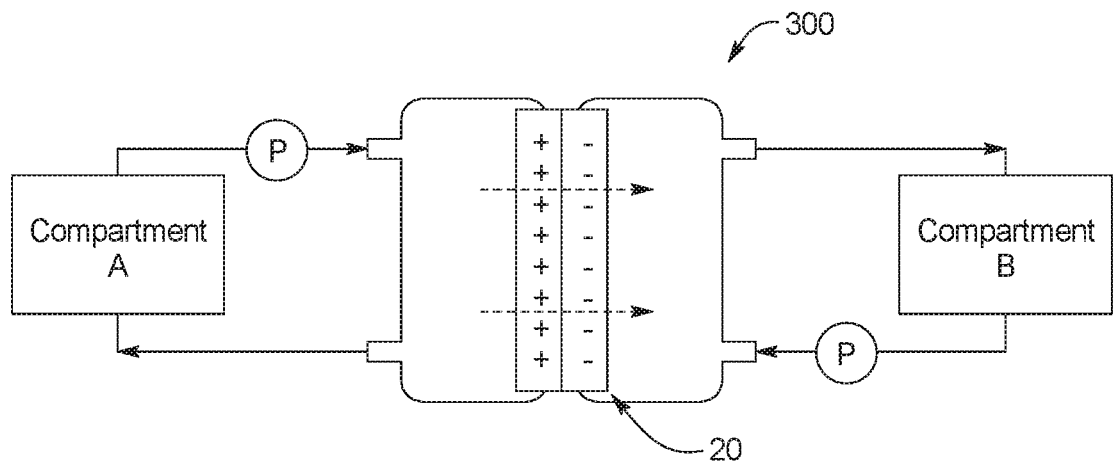
FIG. 11 illustrates a system used to perform several experiments in accordance with the present disclosure.

Several experiments have been performed to confirm that the system of the present disclosure is able to selectively transport urea across a charged membrane while simultaneously rejecting undesired substances. FIG. 11 illustrates a system 300 used in the experiments. As illustrated, experimental system 300 includes Compartment A and Compartment B, which are separated by a urea separation unit 20 as described above.

Experiment 1: Urea Separation Using a Bipolar Membrane

In a first experiment described in connection with FIG. 12 and Table 1, a Fumasep® FBM bipolar membrane was placed into a Sterlitech® CF042-FO membrane cell to create the urea separation unit 20 (FIG. 1). The Fumasep® FBM bipolar membrane is composed of a cation-exchange membrane laminated together with an anion-exchange membrane, through an intermediate layer. The active membrane area of the bipolar membrane was 42 $cm^2$. 350 mL of a 5 g/L urea solution in water was circulated through the fluid circuit including Compartment A, while 350 mL of a 2.9 g/L sodium chloride solution was circulated through the fluid circuit including Compartment B. A sodium chloride solution was chosen for Compartment B due to its high conductivity, while the urea solution was mixed with water and therefore had little or no conductivity. Pumps P in FIG. 11 circulated the urea solution and the sodium chloride solution in a counter current manner at a fixed flow rate of 300 mL/min. The negatively charged side of the bipolar membrane faced the fluid circuit with Compartment B. The experiment was performed at room temperature.

Table 1 below shows the measurements taken within Compartment A and Compartment B during the experiment.

TABLE 1

| Time minutes | Compartment A | | Compartment B | |
|---|---|---|---|---|
| | Urea mg/L | Conductivity μS/cm | Urea mg/L | Conductivity μS/cm |
| 0 | 5025 | 9 | 0 | 5659 |
| 120 | 5395 | — | 41 | 5593 |
| 180 | 4940 | 78 | 68 | 5429 |
| 1410 | 4575 | 98 | 535 | 6058 |

Figure 12:
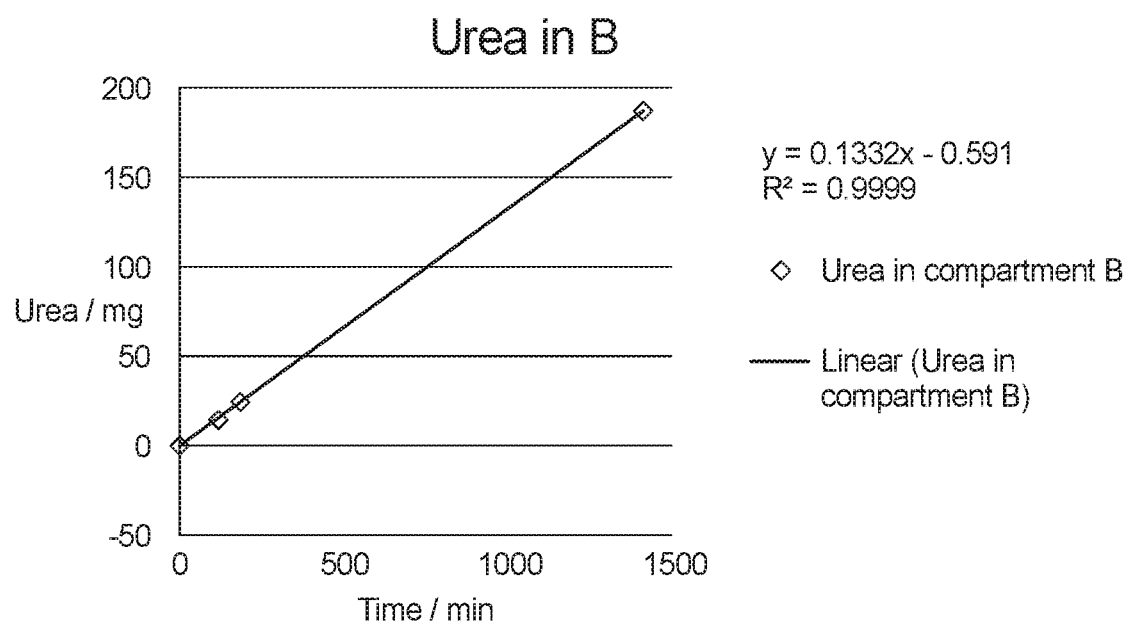
FIG. 12 illustrates experimental data collected using the system of FIG. 11.

FIG. 12 demonstrates that urea diffused through the bipolar membrane at a rate of 0.1332 mg/min, or $3.2 \times 10^{-3}$ mg/min/cm² taking into account that the bipolar membrane had an active surface area of 42 cm². The small change in conductivity observed in Compartment A suggests that the diffusion of electrolytes from Compartment B to Compartment A was prevented or at least significantly reduced due to electrostatic repulsion.

It should be noted that the urea in Compartment A initially increased from 5025 mg/L to 5395 mg/L as illustrated in Table 1 above. Without being bound to any particular theory, it is believed that the urea was initially absorbed by the bipolar membrane at 0 minutes but returned to equilibrium within the fluid circuit including Compartment A once all of the pores of the bipolar membrane had been sufficiently wetted. It is speculated that this is why the measurement of urea concentration at 120 minutes registered higher than the measurement of urea concentration at zero minutes.

It should also be noted that the concentration of urea in Compartment A is substantially higher than what the concentration would be for an actual dialysis treatment. A typical dialysis treatment would remove about 600 mg/L of urea through urea separation unit 20. In the present experiment, a substantially higher concentration of urea was used because the present experiment sought to show that urea would diffuse from Compartment A to Compartment B, but that electrolytes would not diffuse from Compartment B to Compartment A.

It should be noted further that the present experiment tested the concept, but did not optimize the bipolar membrane for treatment. As shown in Table 1, the experiment ran for 1410 minutes to remove 820 mg/L of urea from Compartment A between the 120 minute mark and the 1410 minute mark. The 42 cm² surface area of the bipolar membrane, however, is smaller than what would be used in a system according to the present disclosure. The diffusion rate of urea across the bipolar membrane could be increased substantially, for example, by reducing the thickness of the bipolar membrane (e.g., by eliminating the intermediate layer of the bipolar membrane), by increasing the active surface area of the bipolar membrane, and/or by optimizing the pore size of the bipolar membrane.

The experiment showed that the bipolar membrane was effective at diffusing urea, while preventing the undesired transport of electrolytes due to electrostatic repulsion. Without being bound to any particular theory, it is believed that the minor increase in conductivity within Compartment A and Compartment B over the course of the experiment may have been due to carbon dioxide being captured in the compartments during the experiment. It is also expected that the conductivity values oscillated over the course of the experiment.

Experiment 2: Urea Separation from a Simulated Peritoneal Dialysis Solution Using Bipolar Membrane In a second experiment described in connection with FIGS. 13 and 14 and Table 2, a Fumasep® FBM bipolar membrane was placed into a Sterlitech® CF042-FO membrane cell to create the urea separation unit 20 (FIG. 1). The active membrane area of the bipolar membrane was 42 cm². 350 mL of a 600 mg/L solution of urea in peritoneal dialysis solution (with 2.5% glucose) was circulated through the fluid circuit including Compartment A, while 350 mL of a sodium chloride solution was circulated through the fluid circuit including Compartment B. Pumps P in FIG. 11 circulated the urea solution and the sodium chloride solution in a counter current manner at a fixed flow rate of 300 mL/min. The negatively charged side of the bipolar membrane faced the fluid circuit with Compartment B. The experiment was performed at room temperature.

Table 2 below shows the measurements taken within Compartment A and Compartment B during the experiment.

TABLE 2

| Time minutes | Compartment A | | | | | Compartment B | | | | |
|---|---|---|---|---|---|---|---|---|---|---|
| | Urea mg/L | Conductivity μS/cm | $Ca^{2+}$ mg/L | $Mg^{2+}$ mg/L | Glucose mg/L | Urea mg/L | Conductivity μS/cm | $Ca^{2+}$ mg/L | $Mg^+$ mg/L | Glucose mg/L |
| 0 | 585 | 10454 | 93 | 12 | 22800 | 1 | 11359 | 0.0 | 0.0 | 0 |
| 150 | 657 | 10471 | 93 | 14 | 22620 | 5 | 10867 | 0.0 | 0.0 | 5 |
| 218 | 644 | 9181 | 94 | 14 | 22440 | 5 | 10839 | 0.0 | 0.0 | 10 |
| 300 | 653 | 9483 | 93 | 14 | 22480 | 8 | 10752 | 0.0 | 0.0 | 10 |
| 1370 | 589 | 10293 | 95 | 23 | 22440 | 28 | 11677 | 1.0 | 1.0 | 70 |

Table 2 demonstrates that the diffusion of $Ca^{2+}$ and $Mg^+$ through the bipolar membrane was negligible, as both ions were effectively rejected by the bipolar membrane.

Figure 13:
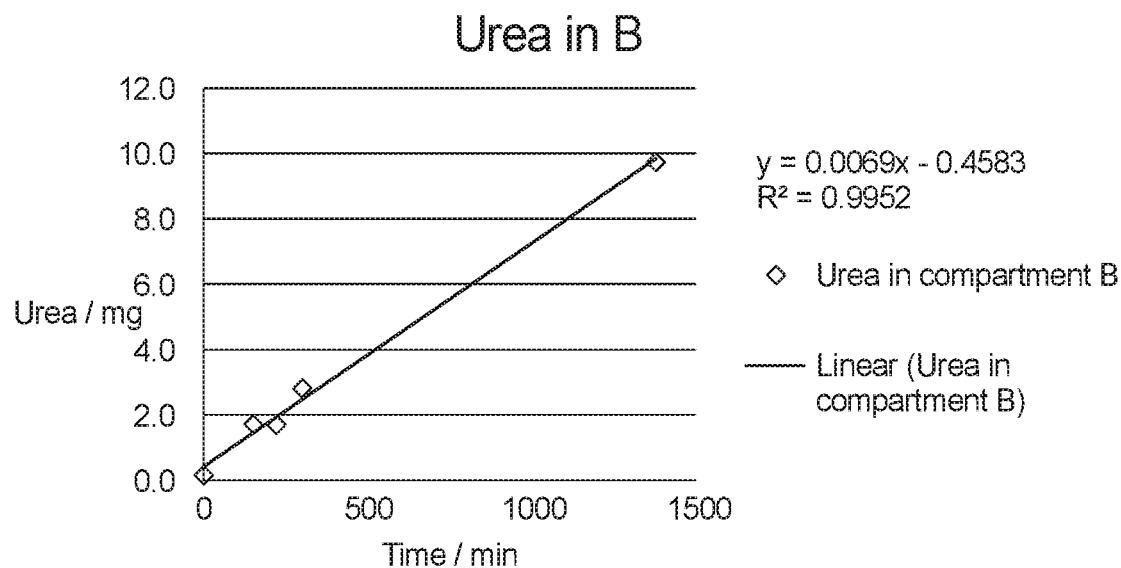
FIG. 13 illustrates experimental data collected using the system of FIG. 11.

FIG. 13 demonstrates that urea diffused through the bipolar membrane at a rate of 0.0069 mg/min, or $1.6 \times 10^{-4}$ mg/min/cm² taking into account that the bipolar membrane had an active surface area of 42 cm².

Figure 14:
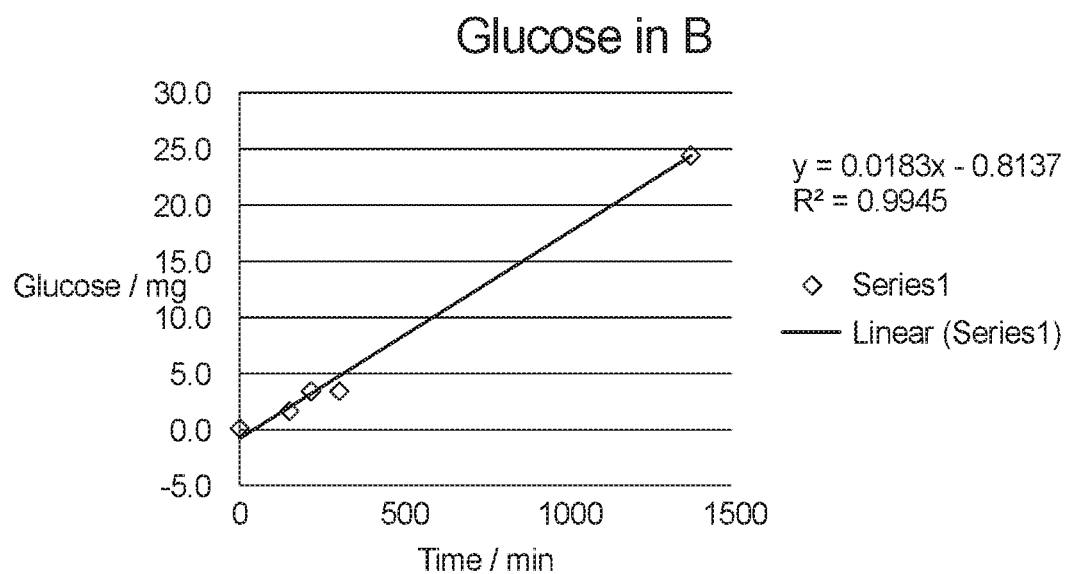
FIG. 14 illustrates experimental data collected using the system of FIG. 11.

In this experiment, a very large amount of glucose was used in Compartment A to magnify the glucose transport across the bipolar membrane. FIG. 14 demonstrates that a small diffusion of glucose across the bipolar membrane was observed at a rate of $4.4 \times 10^{-4}$ mg/min/cm². It is important to note that the amount of glucose transported across the bipolar membrane was in the same order of magnitude as urea, despite the significantly higher concentration gradient for glucose. The concentration gradient for glucose in Compartment A (22.8 g/L) was approximately 38 times higher than the concentration of urea (0.6 g/L), indicating that the system does indeed transport urea across the membrane more freely, with only a minor amount of glucose transporting across the bipolar membrane.

Although the urea transport appears low in the experiment, it should be noted that the purpose of the experiment was to show that $Ca^{2+}$, $Mg^+$ and glucose would not transport through the bipolar membrane. As explained above, the 42 cm² surface area of the bipolar membrane is smaller than what would be used in a system according to the present disclosure. The diffusion rate of urea across the bipolar membrane could be increased substantially, for example, by reducing the thickness of the bipolar membrane (e.g., by eliminating the intermediate layer of the bipolar membrane), by increasing the active surface area of the bipolar membrane, and/or by optimizing the pore size of the bipolar membrane.

Experiment 3: Urea Separation Using Bipolar Membrane and High pH Urea Removal Solution In a third experiment described in connection with FIGS. 15 and 16 and Tables 3 and 4, a Fumasep® FBM bipolar membrane was placed into a Sterlitech® CF042-FO membrane cell to create the urea separation unit 20 (FIG. 1). The active membrane area of the bipolar membrane was 42 cm². 350 mL of a urea solution was circulated through the fluid circuit including Compartment A, while 350 mL of a sodium hydroxide/sodium chloride solution was circulated through the fluid circuit including Compartment B. The urea solution and the sodium hydroxide/sodium chloride solution were circulated in a counter current manner via pumps P in FIG. 11 at a fixed flow rate of 300 mL/min. The negatively charged side of the bipolar membrane faced the fluid circuit with Compartment B. The experiment was performed at room temperature.

Tables 3 and 4 below show the measurements taken within Compartment A and Compartment B during the experiment.

TABLE 3

| Compartment | Urea g/L | NaCl g/L | NaOH g/L |
|---|---|---|---|
| A | 6 | 0 | 0 |
| B | 0 | 2.3 | 0.4 |

TABLE 4

| | Compartment A | | | Compartment B | | |
|---|---|---|---|---|---|---|
| Time minutes | Urea mg/L | Conductivity µS/cm | pH | Urea mg/L | Conductivity µS/cm | pH |
| 0 | 5842 | 15 | 7.2 | 1 | 3694 | 12.2 |
| 65 | 6035 | 44 | 6.8 | 27 | 3704 | 12.0 |
| 155 | 5671 | 42 | 6.5 | 60 | 3671 | 12.0 |
| 1230 | 5404 | 83 | 6.5 | 480 | 5695 | 12.0 |

The purpose of the third experiment was to demonstrate the effect of having a high pH solution circulating on one side of the membrane. As explained above, for example, an electrooxidation unit more effectively oxidizes urea when the pH of the secondary fluid containing urea is basic, so it may be preferable to raise the pH of the secondary fluid flowing through urea circuit 60 described above. It is important, however, for the urea separation unit 20 to prevent hydroxide ions from the electrooxidation process from transporting across the membrane and into the dialysis fluid in the dialysis fluid circuit.

Figure 15:
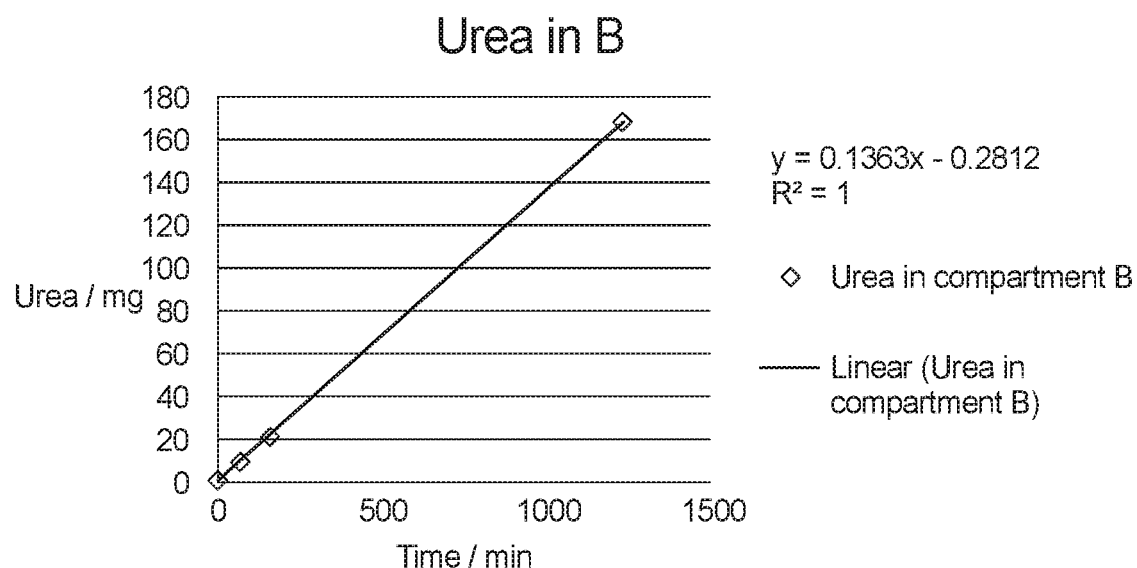
FIG. 15 illustrates experimental data collected using the system of FIG. 11.

FIG. 15 demonstrates that urea diffused through the bipolar membrane at a rate of 0.1363 mg/min, or $3.2 \times 10^{-3}$ mg/min/cm² taking into account that the bipolar membrane had an active surface area of 42 cm². The small change in conductivity observed in Compartment A suggests that the diffusion of electrolytes from Compartment B to Compartment A was prevented or at least significantly reduced due to electrostatic repulsion. It should be noted that the conductivity increased from 42 µS/cm to 83 µS/cm between the 155 minute mark and the 1230 minute mark. This represents a relatively minor increase in conductivity, as any value below 100 µS/cm is considered low for conductivity. It is also expected that the conductivity values oscillated over the course of the experiment.

Figure 16:
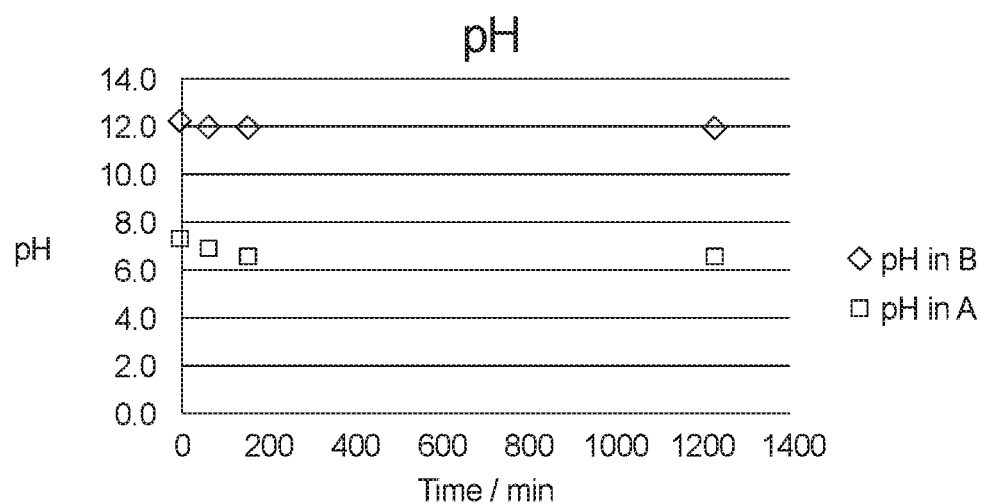
FIG. 16 illustrates experimental data collected using the system of FIG. 11.

FIG. 16 demonstrates that the pH on both sides of the bipolar membrane remained stable during the experiment, confirming that the bipolar membrane effectively prevents hydroxide ions from diffusing from Compartment B to Compartment A.

In the above three experiments, it was determined that a bipolar membrane is effective as the membrane 26, 222 of the present disclosure. It is contemplated that other membranes will also be effective, for example, if optimized for hydrophilicity, thickness, active surface area, charged density, pore size and/or pore distribution.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details may be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A regenerative dialysis fluid system comprising:
a dialysis unit;
a peritoneal dialysis cassette operable with the dialysis unit and configured to enable pumping of used dialysis fluid including urea from a patient;
a urea separation unit including (a) a dialysis fluid chamber configured to receive the used dialysis fluid from the peritoneal dialysis cassette, and (b) a urea chamber, the urea separation unit configured to separate at least a portion of the urea from the used dialysis fluid into a secondary fluid located within the urea chamber and return the used dialysis fluid with the at least the portion of the urea separated through the peritoneal dialysis cassette; and
a urea removal unit configured to receive the secondary fluid with the separated urea from the urea chamber, remove at least a portion of the urea from the secondary fluid, and return at least some of the secondary fluid to the urea chamber of the urea separation unit,
wherein the peritoneal dialysis cassette is fluidly coupled to the urea separation unit to enable pumping of the used dialysis fluid to the urea separation unit.

2. The regenerative dialysis fluid system of claim 1, wherein the dialysis unit includes at least one pump actuator and the peritoneal dialysis cassette includes at least one pumping chamber for operation respectively with the at least one pump actuator, the at least one pumping chamber configured for pumping the used dialysis fluid to the urea separation unit.

3. The regenerative dialysis fluid system of claim 2, further comprising a patient line fluidly coupling a peritoneal cavity of a patient to the at least one pumping chamber of the peritoneal dialysis cassette.

4. The regenerative dialysis fluid system of claim 2, further comprising a collection container fluidly coupled to the at least one pumping chamber of the peritoneal dialysis cassette, the collection chamber configured to receive the used dialysis fluid from the patient.

5. The regenerative dialysis fluid system of claim 4, wherein the dialysis unit includes a control unit configured to control the at least one pump actuator,
wherein the control unit is configured to:
(i) cause the peritoneal dialysis cassette to pump the used dialysis from the collection container to the dialysis fluid chamber of the urea separation unit for separating the at least the portion of the urea from the used dialysis fluid, and
(ii) cause the peritoneal dialysis cassette to pump the used dialysis fluid with the at least the portion of the urea separated from the urea separation unit to the collection container or another collection container as regenerated dialysis fluid.

6. The regenerative dialysis fluid system of claim 5, wherein the control unit is configured to cause the regenerated dialysis fluid to be pumped to the patient for a next dialysis treatment.

7. The regenerative dialysis fluid system of claim 5, wherein the control unit is configured to repeat (i) and (ii) a number of times to produce the regenerated dialysis fluid.

8. The regenerative dialysis fluid system of claim 1, wherein the dialysis unit is a peritoneal dialysis unit.

9. The regenerative dialysis fluid system of claim 1, wherein the urea separation unit includes a membrane separating the dialysis fluid chamber from the urea chamber, and
wherein the membrane includes at least one of:
(i) a positive charge to prevent positive ions of at least one of the used dialysis fluid or the secondary fluid from transporting across the membrane between the dialysis fluid chamber and the urea chamber, or
(ii) a negative charge to prevent negative ions of at least one of the used dialysis fluid or the secondary fluid from transporting across the membrane between the dialysis fluid chamber and the urea chamber.

10. The regenerative dialysis fluid system of claim 9, wherein the membrane includes an anion exchange membrane ("AEM") and a cation exchange membrane ("CEM"), the AEM providing the positive charge and the CEM providing the negative charge.

11. A regenerative dialysis fluid system comprising:
a dialysis cassette including at least one pumping chamber for pumping used dialysis fluid including urea from a patient;
a urea separation unit including (a) a dialysis fluid chamber configured to receive the used dialysis fluid from the dialysis cassette, and (b) a urea chamber, the urea separation unit configured to separate at least a portion of the urea from the used dialysis fluid into a secondary fluid located within the urea chamber and return the used dialysis fluid with the at least the portion of the urea separated through the dialysis cassette; and
a urea removal unit configured to receive the secondary fluid with the separated urea from the urea chamber, remove at least a portion of the urea from the secondary fluid, and return at least some of the secondary fluid to the urea chamber of the urea separation unit,
wherein the dialysis cassette is fluidly coupled to the urea separation unit for pumping the used dialysis fluid to the urea separation unit.

12. The regenerative dialysis fluid system of claim 11, wherein the dialysis cassette is configured for pumping the used dialysis fluid with the at least the portion of the urea separated from the urea separation unit to at least one collection chamber for a next dialysis treatment.

13. The regenerative dialysis fluid system of claim 12, wherein the dialysis cassette:
pumps the used dialysis fluid from the patient to the at least one collection chamber after a dialysis treatment that is before the next dialysis treatment, and
pumps the used dialysis fluid from the at least one collection chamber to the urea separation unit.

14. The regenerative dialysis fluid system of claim 11, wherein the dialysis cassette includes a first pumping chamber for pumping the used dialysis fluid and a second pumping chamber for pumping the used dialysis fluid with the at least the portion of the urea separated.

15. The regenerative dialysis fluid system of claim 11, wherein the dialysis cassette includes a pump chamber for pumping the secondary fluid with the separated urea from the urea chamber to the urea removal unit.

16. The regenerative dialysis fluid system of claim 15, wherein the pump chamber of the dialysis cassette is configured to cause the at least some of the secondary fluid to be returned to the urea chamber of the urea separation unit from the urea removal unit.

17. The regenerative dialysis fluid system of claim 11, wherein the urea separation unit includes a membrane separating the dialysis fluid chamber from the urea chamber.

18. The regenerative dialysis fluid system of claim 17, wherein the membrane includes pores sized between about 5 nm and 10 μm.

19. The regenerative dialysis fluid system of claim 11, wherein the urea removal unit includes at least one of a chemical adsorption device, an electrooxidation device, or an enzymatic oxidation device, and
wherein the urea removal unit is configured to collect or discard the urea removed from the secondary fluid.

* * * * *